US006607527B1

(12) United States Patent
Ruiz et al.

(10) Patent No.: US 6,607,527 B1
(45) Date of Patent: Aug. 19, 2003

(54) METHOD AND APPARATUS FOR PRECISION LASER SURGERY

(76) Inventors: Luis Antonio Ruiz, Centro Ofialmólogico Colombiano, Carrera 20 No. 85-11, Pisos 5o-6o, Santaré de Bogotá, D.C. (CO); Eduardo Matallana, Centro Ofialmólogico Colombiano, Carrera 20 No. 85-11, Pisos 5o-6o, Santaré de Bogota, D.C. (CO); Arnoldo Narvaez, Centro Ofialmólogico Colombiano, Carrera 20 No. 85-11, Pisos 5o-6o, Santaré de Bogota, D.C. (CO)

( * ) Notice: Subject to any disclaimer, the term of this patent is extended or adjusted under 35 U.S.C. 154(b) by 38 days.

(21) Appl. No.: 09/688,382

(22) Filed: Oct. 17, 2000

(51) Int. Cl.[7] ................................................ A61B 18/18
(52) U.S. Cl. ............................... 606/41; 606/5; 606/10; 351/212
(58) Field of Search ............................... 606/41, 3, 4, 5, 606/7, 10, 11, 166; 351/211, 212, 208, 221, 205, 206, 246

(56) References Cited

U.S. PATENT DOCUMENTS

| 4,631,583 A | 12/1986 | Paul .......................... 358/125 |
| 4,848,340 A | 7/1989 | Bille et al. ............... 128/303.1 |
| 4,881,080 A | 11/1989 | Jablonski |

(List continued on next page.)

FOREIGN PATENT DOCUMENTS

| DE | 42 32 021 A | 4/1994 |
| EP | 0 765 648 A | 4/1997 |
| EP | 0 770 370 A | 5/1997 |
| WO | WO 93 08877 A | 5/1993 |
| WO | WO 95 28989 A | 11/1995 |
| WO | WO 99 23936 A | 5/1999 |
| WO | 99/26242 | 5/1999 |
| WO | WO 99 54783 A | 10/1999 |
| WO | WO 99 55216 A | 11/1999 |
| WO | WO 00 21475 A | 4/2000 |
| WO | 00/21475 | 4/2000 |
| WO | WO 00/27273 A | 5/2000 |
| WO | 00/27324 | 5/2000 |

OTHER PUBLICATIONS

Internet Product Information from Carl Zeiss Inc. describing KL 200, KL 1500 LCD/KL 2500 LCD light sources; date of publication unknown.

"Edmund Industrial Optics and Optical Instruments Catalog"; cover sheet and pp. 218–220, 222 and 223; copyright notice date of 1999.

*Primary Examiner*—Teresa Walberg
*Assistant Examiner*—Fadi H. Dahbour
(74) *Attorney, Agent, or Firm*—Smith, Gambrell & Russell

(57) ABSTRACT

An eye laser system which includes a laser and a laser delivery system for delivering a laser beam generated by the laser to the eye and an eyetracking system which monitors movement of the eye and conveys eyetracking information to the laser delivery system with the eyetracking system including a non-invasive eye tilt reference marker. The reference marker projects an energy beam that is preferably visible so as to reflect off the iris of the eye and provide microscope and surgical field illumination. The reference marker includes a plurality of points arranged concentrically about the pupil of the eye and/or a concentric ring marking device. This arrangement provides information as to eye tilt for use in, for example, video frame review during an initial reference setting or a subsequent eye tracking stage. Also described are laser delivery systems including an eye tilt accommodation laser delivery systems that are well suited for use with the eyetracking system described above which provides an indication of eye tilt and provide data sufficient for determining an angle of eye tilt and hence an angle required by the laser accommodating system to provide a laser beam coincident with the axis of tilt for a tilted eye.

32 Claims, 28 Drawing Sheets

U.S. PATENT DOCUMENTS

| | | |
|---|---|---|
| 5,029,220 A | 7/1991 | Juday .............................. 382/6 |
| 5,098,426 A | 3/1992 | Sklar et al. ..................... 606/5 |
| 5,133,726 A * | 7/1992 | Ruiz et al. ................. 606/166 |
| 5,162,641 A | 11/1992 | Fountain .................. 250/201.2 |
| 5,533,997 A | 7/1996 | Ruiz .............................. 606/5 |
| RE35,421 E * | 1/1997 | Ruiz et al. ................. 606/166 |
| 5,620,436 A | 4/1997 | Lang et al. .................... 606/4 |
| 5,782,822 A * | 7/1998 | Telfair et al. .................. 606/5 |
| 5,807,381 A * | 9/1998 | Lieberman ..................... 606/5 |
| 5,928,129 A | 7/1999 | Ruiz .............................. 600/5 |
| 5,980,513 A | 11/1999 | Frey et al. .................... 606/10 |
| 6,099,522 A | 8/2000 | Knopp et al. |
| 6,129,722 A | 10/2000 | Ruiz .............................. 606/5 |
| 6,149,609 A * | 11/2000 | Lieberman et al. ............ 606/5 |
| 6,217,570 B1 * | 4/2001 | Nevyas .......................... 606/5 |
| 6,227,667 B1 * | 5/2001 | Halldorsson et al. ....... 351/206 |
| 6,299,309 B1 | 10/2001 | Ruiz |
| 6,302,877 B1 * | 10/2001 | Ruiz .............................. 606/5 |

\* cited by examiner

FIG. 7A
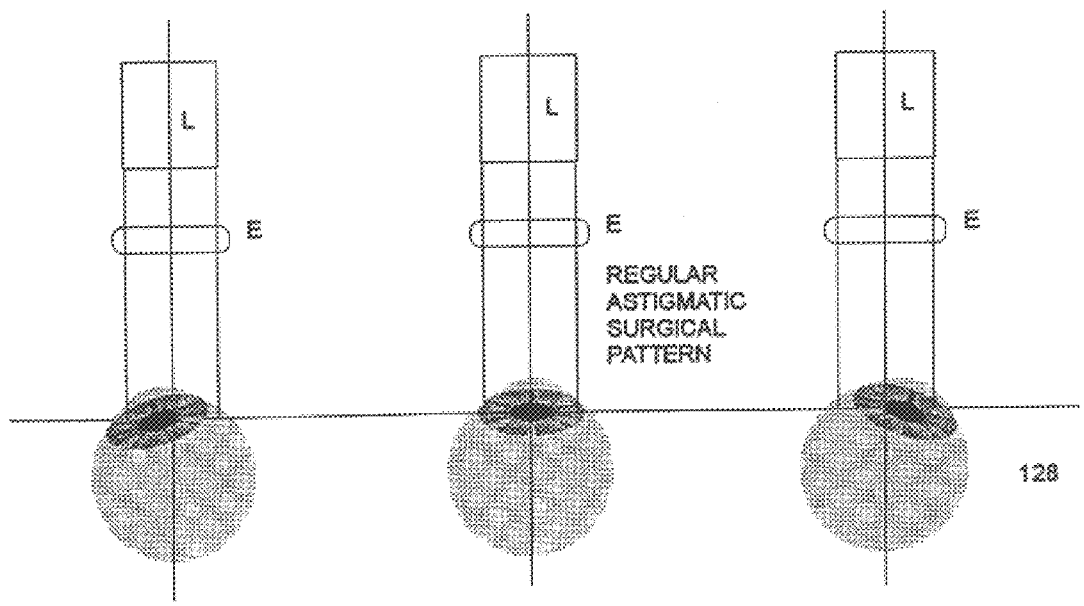
FIG. 7B
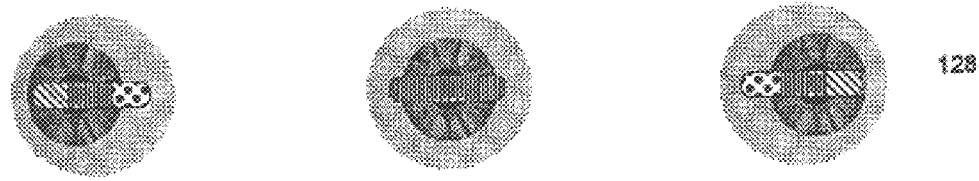
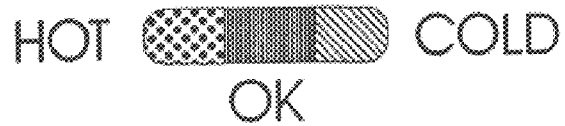

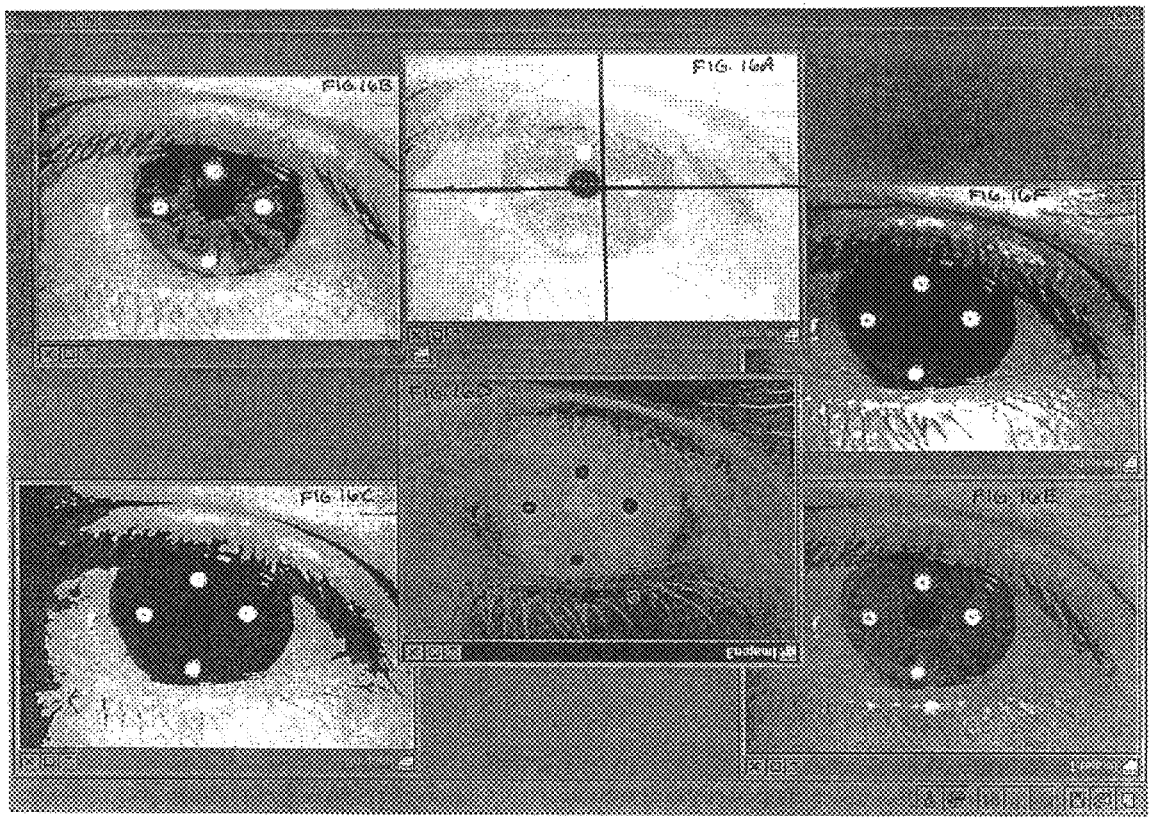

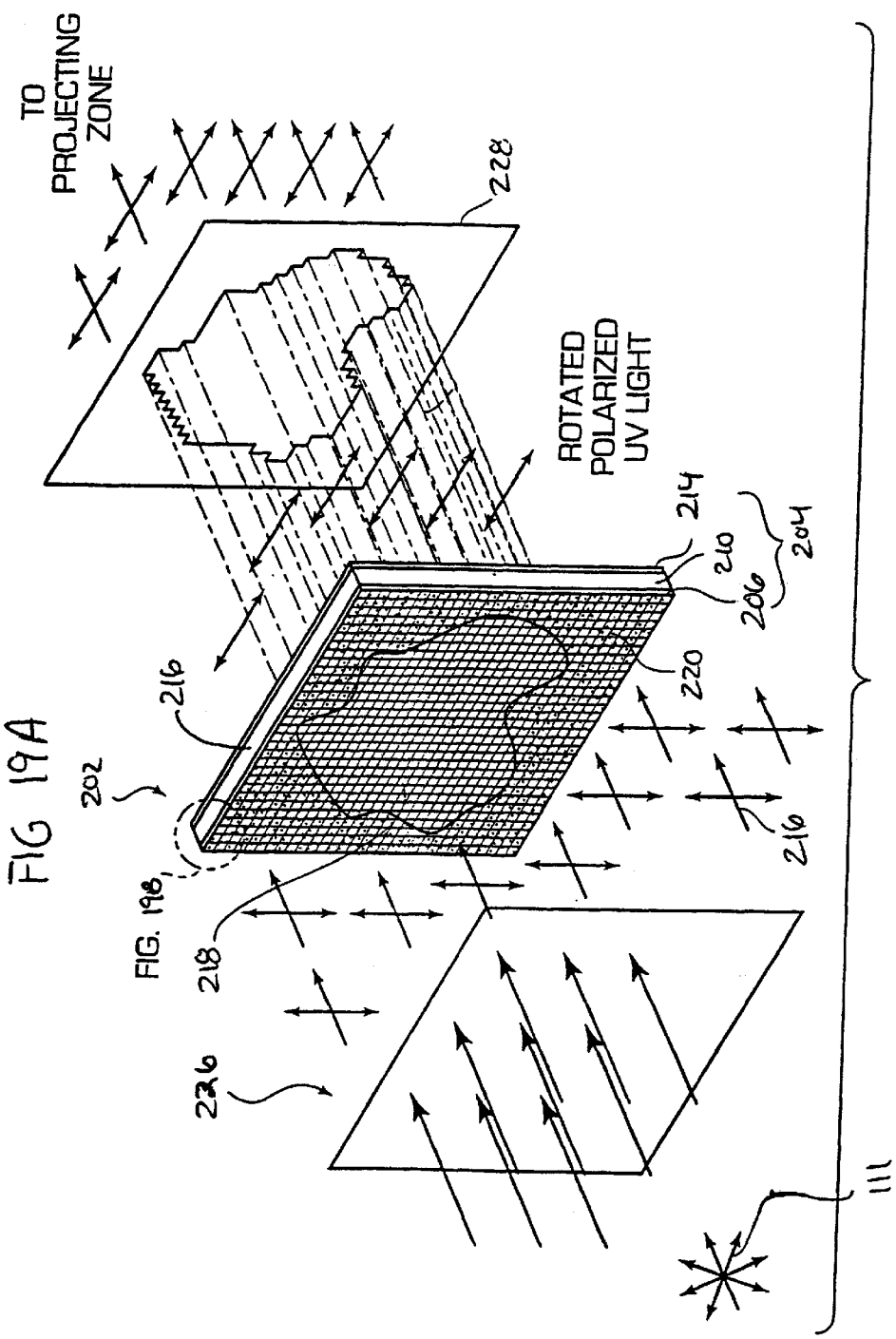
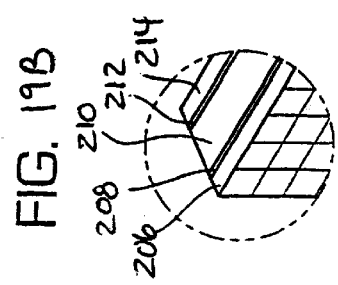

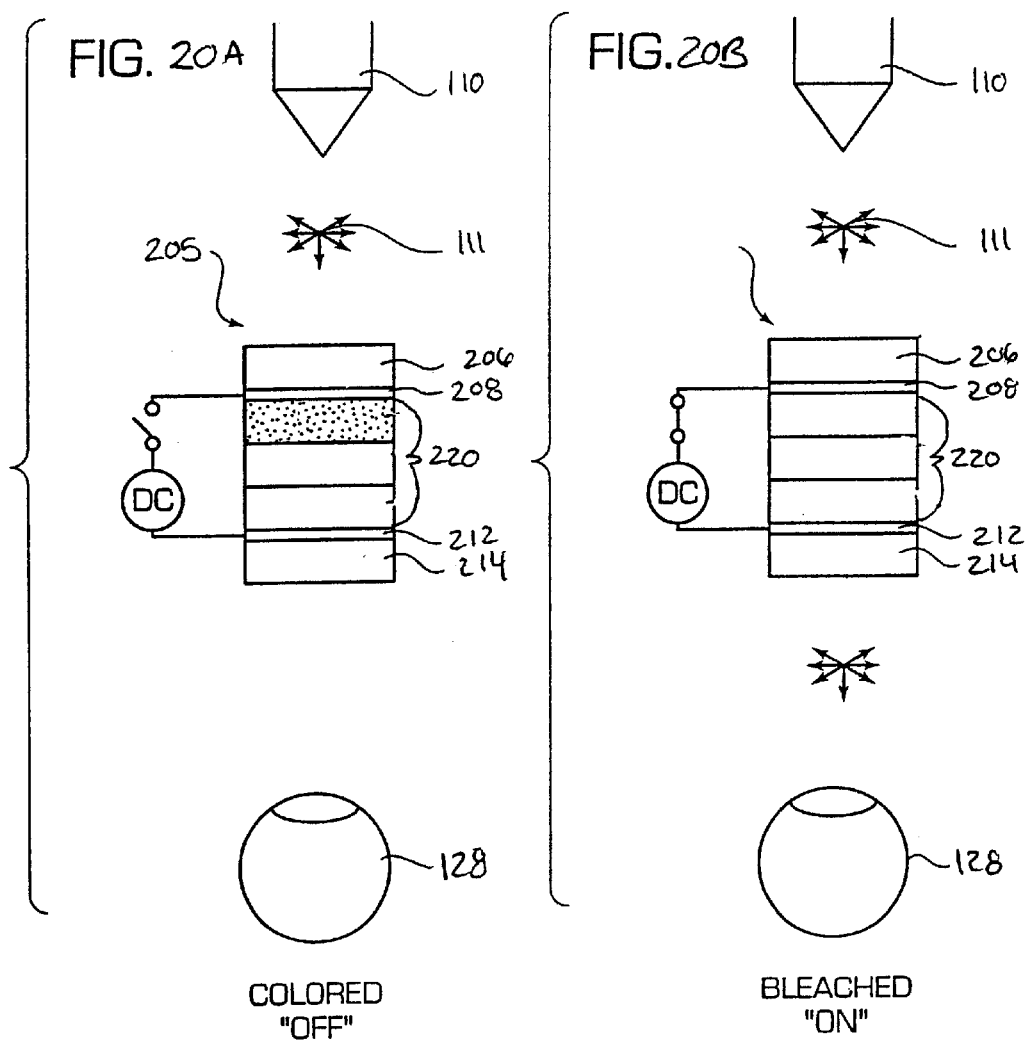
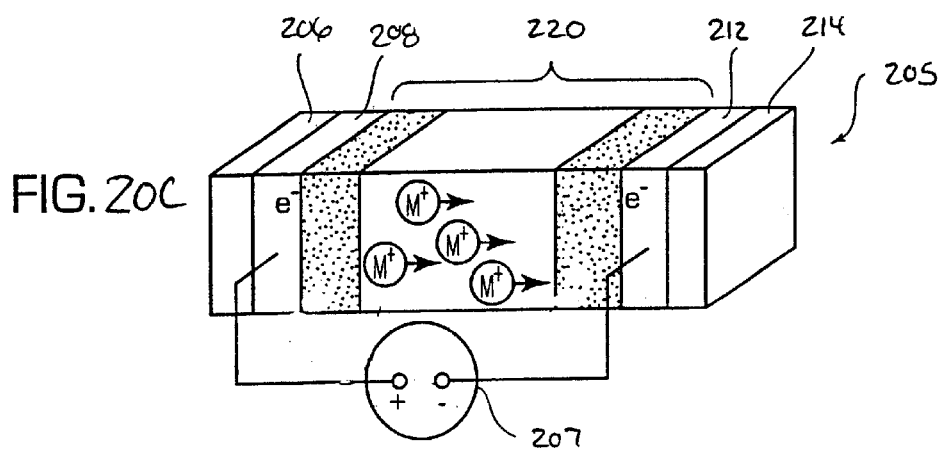

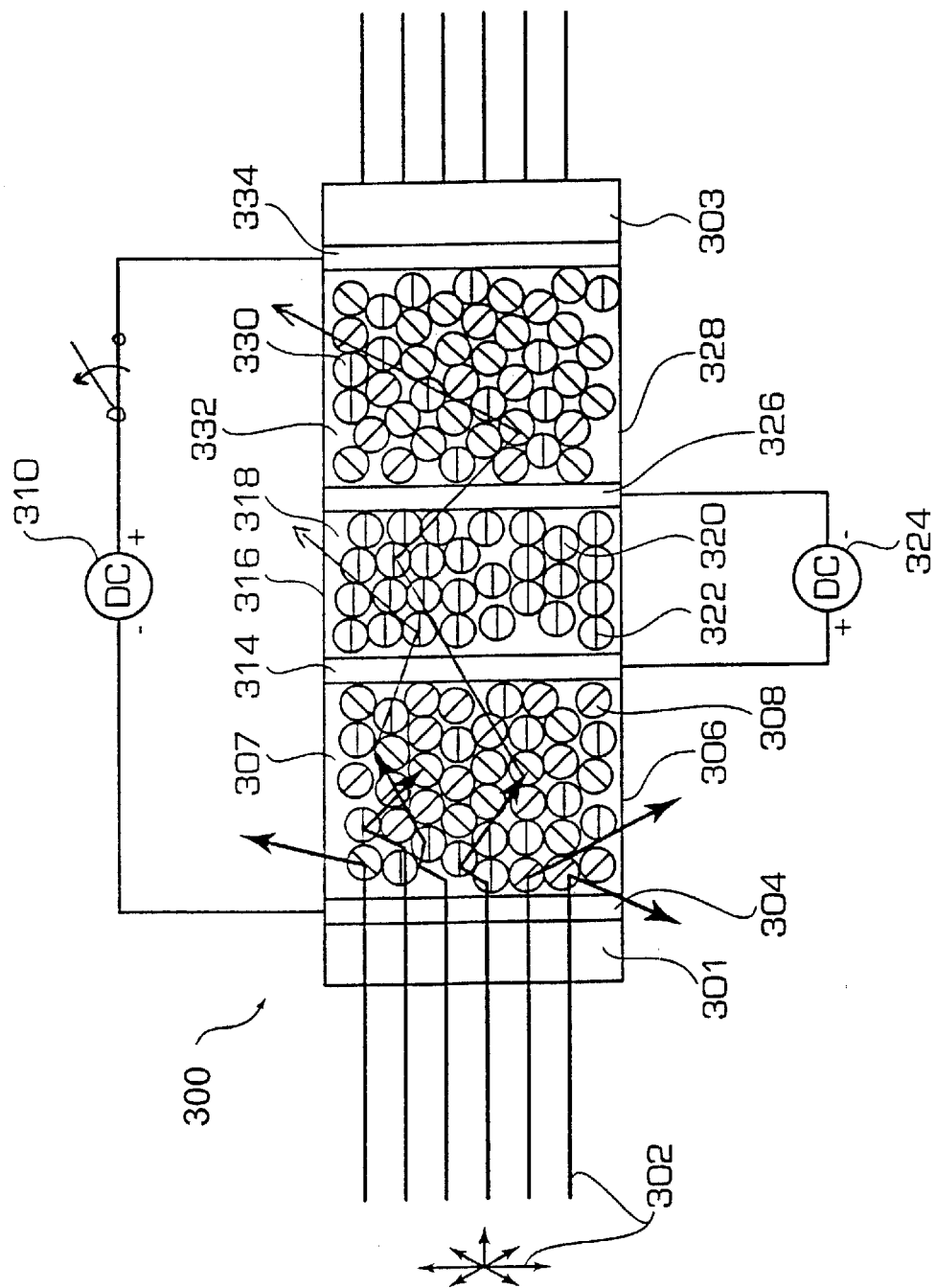

METHOD AND APPARATUS FOR PRECISION LASER SURGERY

FIELD OF THE INVENTION

The present invention is directed at a precision ophthalmic surgical laser method and system and includes an active eyetracker system and method for accurate and efficient eyetracking which takes into consideration eye tilt, and laser delivery systems and methods well suited for accommodating eye tilt during laser application.

BACKGROUND OF THE INVENTION

Roughly two decades ago, surgical techniques were introduced in an effort to permanently correct shortsightedness and astigmatism. The radial keratotomy procedure used a diamond blade to make incisions into the cornea, the front surface or "window of the eye". Although this technique worked relatively well, there have been problems with long term stability of vision and weakening of the cornea as a result of the cuts often having to be made up to 95% of the corneal thickness.

More recently, these older techniques have been replaced with laser treatment techniques which have replaced the surgeon's blade with a computer controlled laser that gently re-sculptures the shape of the cornea without cutting or, for most applications, weakening the eye. These laser techniques are typically carried out with a photoablation process using an excimer laser.

An excimer laser's extreme accuracy and low thermal effect makes it well suited as an eye laser. Many eye lasers are extremely accurate and remove only 0.25 microns ($1/4000^{th}$ millimeter) of tissue per pulse. During corneal re-sculpturing, the excimer laser gently "evaporates" or vaporizes tissue; there is no burning or cutting involved. In the normal eye, light rays entering the eye are accurately focused on the retina and a clear image is formed. Most of the bending or focusing of the light rays occurs at the cornea, with the natural lens inside the eye being responsible for fine adjustments. If light is not focused on the retina, then the eye is said to have a refractive error. Common refractive errors include: myopia or shortsightedness, hyperopia or farsightedness, and astigmatism. The excimer laser has been used to re-sculpture the cornea in myopia, hyperopia and astigmatism corrections in an effort to make the curvature of the cornea focus light rays normally on the retina.

Presbyopia is a problem considered to be due to an aging process occurring in the natural lens of the eye, and thus does not fall under the same category as the refractive errors of myopia, astigmatism and hyperopia noted above, although combinations of presbyopia and one or more of the refractive errors are possible. U.S. Pat. Nos. 5,533,997 and 5,928,129 to Dr. Luis A. Ruiz describe presbyopia corrective apparatus and methods which involve the use of a laser system to remove tissue from the eye in presbyopic corrective patterns discovered to be effective by Dr. Ruiz. These two patents are incorporated herein by reference. Reference is also made to PCT Publication No. WO 00/27324 for International Application No. PCT/US99/26242 filed on Nov. 8, 1999, directed at improvement in presbyopia "LASIK" surgery. This PCT publication is also incorporated herein by reference and represents further improvement in addressing presbyopia by way of laser surgery.

Also, the corneal surface is not a very smooth body and has topographical irregularities which can be both large and small. Under prior art laser systems these surface irregularities are not fully taken into consideration in the standard formulas and patterns designed to correct defects such as hyperopia, myopia and astigmatism. Accordingly, the final ablation profile formed in the eye deviates to some extent from what was predetermined by the surgeon to be the final resultant profile of the eye, and this is particularly true with respect to eyes with highly irregular surfaces wherein the defect can be simply shifted to a lower corneal altitude and thus create a new defect which is often unpredictable under the prior art systems. Reference is made to U.S. Pat. No. 6,129,722 which issued on Oct. 10, 2000 and is incorporated herein by reference. U.S. Pat. No. 6,129,722 describes improvements in eye ablation volume formation in laser eye surgery that takes into consideration the topographic irregularities in the eye being ablated, while also allowing for the input of the surgeons expertise.

Reference is also made to co-pending U.S. Ser. Nos. 09/598,226 and 09/598,227 each filed on Jun. 21, 2000 to Dr. Luis Ruiz and Eduardo Matallana which are incorporated by reference herein. These applications describe means for enhancing accuracy, registration and desired beam density application to conform the applied ablation volume pattern with the desired vision enhancements through use of an active mask in the path of the laser beam.

Despite the above described improvements in determining the desired ablation volume to be applied and providing a laser system capable of achieving high precision with respect to the desired ablation volume pattern, if the laser can not keep up with movement of the eye, including eye tilt about its normal axis, than all the enhancements in these other areas will be lost or degraded in the final result.

Efforts have been made in the prior art to improve the tracking response of a laser with eye movements. Laser systems without an eyetracker system rely on having patients fixate their gaze upon a fixation light. This technique does not, however, prevent rapid movements of the eye. Further, a momentary lapse in fixation can result in an ablation shot far from the intended shot location. As an alternative, physical fixation devices have been used which immobilize the eye by physically connecting to the eye, thereby holding it steady. This technique can lead to increased patent discomfort and a further cluttering of the surgical area.

More recent techniques involve computer aided eyetracking devices. These tracking devices are typically optical or topographic location systems that use a video camera to either optically or topographically locate and track the center of the eye. Examples of such systems can be found in U.S. Pat. No. 5,602,436 to Lang et al., U.S. Pat. No. 5,098,426 to Sklar et al., U.S. Pat. No. 5,162,641 to Fountain and U.S. Pat. No. 4,848,340 to Bille. These systems use various techniques to track the center of the eye, such as a computer mapped digital image from a video camera. For example, U.S. Pat. No. 5,098,426, to Sklar, et al., hereby incorporated by reference, describes an eyetracking system that generates a three dimensional profile of the eye and tracks movement by noting changes in that profile. The Sklar patent shows an eyetracker using a slow control loop and a fast control loop. The slow control loop relies on a video camera to provide topographical information that the eyetracker then uses to aim the system optics.

An alternate eyetracking system is shown in U.S. Pat. No. 4,848,340 to Bille, also incorporated by reference. The Bille patent shows a strictly optical, rather than topographical, based system that tracks a reference grid which has been ablated into the eye. U.S. Pat. No. 5,980,513 to Frey et al.

illustrates another example of an eyetracking system and relies on substantial mirror movement requirements.

Some prior art eyetracking systems use infrared light to illuminate the pupil of the eye in an effort to facilitate tracking. One example is found in U.S. Pat. No. 5,620,436 which utilizes an eyetracker system relying on a non coaxial infrared heat source located on a side of a patient for the detection of an infrared heat target normally being the center of the pupil.

The above described systems tend to be either invasive, not particularly accurate and/or complicated, in the sense that they require actual physical markings to be made on the eye ( as shown in the Bille patient), or require highly complex and often not highly accurate topographical location systems and multiple feedback loops for locating the center of the eye. Also, those systems relying on infrared heat sources are very sensitive to changes in the illumination and infrared spectrum contaminations generated by the on/off conditions of the illumination lamps of the microscope and auxiliary lights used by the surgeon during the surgery as well as surgeon generated shadows by his hands and instruments in the operating field or even by the patient morphological constitution.

These illumination changes generated by the on/off and intermediate conditions of the surgical lights when the surgeon uses the microscope usually confuse the eyetracker, oversaturate the video camera, confuse the software and the computer detection algorithms used by these systems creating potentially dangerous situations for the patient and the end result of the surgery.

Another drawback in prior art eyetracker systems are that they are limited by not being able to provide sufficient information in order to have the laser delivery system apply the laser beam precisely where desired with respect to the eye. The deficiencies in the prior art eyetracker systems are especially pronounced when dealing with eye tilting which is a more common situation than X, Y plane shift. The lack of eyetracker systems adequately addressing the problem of tracking eye tilt movement is not surprising in view of the lack of laser delivery systems well suited for accommodating eye tilt. The inability to track eye tilt and provide the appropriate adjustment in the laser beam delivery can lead to undesirable results during the resculpturing of an eye. For example, under a common myopia pattern application wherein a cap is removed based on a basic geometrical ablation volume pattern, there is a tendency in the prior art to induce error in eyes that are tilted at the time of laser application. Much like the seasonal shifts on Earth due to tilting with respect to the sun, the application of a laser beam to a tilted eye induces an unintended variation in energy application over the ablated region such that one portion of the intended ablation pattern receives a greater degree of energy than planned, while another region receives less applied energy than planned. This unintended variation in applied energy due to eye tilting is more pronounced when dealing with large beam laser application systems. An additional problem concerning eye tilt is the potential for an eye tilt to be present at the time of determining initial reference coordinates for video tracking. This initial error in reference determination carries over to all later laser beam applications during an eye ablation process and thus can lead to significant errors. These errors created due to eye tilt clearly appear in a post-op topographical exam.

SUMMARY OF THE INVENTION

The present invention features an active eyetracker system, method and apparatus designed and built to sense and detect variations in the (X), (Y) coordinates as well as to detect any eye tilt. With the eye tilt being detected, for example, by a monitoring of any inclination of the normal axis of the eye from an initial state corresponding with the normal of the optical train to a new position forming an angle with respect to the normal of the optical train axis due to pivoting of the eye within its orbital socket. In a preferred embodiment, the optical eyetracker system uses the strategically positioned regular and auxiliary microscope illumination lights to provide reference marking means that take advantage of the natural ability of the cornea to bend and refract all light, central or peripheral in toward the pupil. It is the bent and refracted light beam that establish the reference markings in accordance with the present invention.

Under the present invention eye tilt tracking is possible through use of a tracking system which utilizes reference marking means such as non-invasive light beam pointer marking devices and/or ring illuminator device(s) that project on to the iris of the eye a reference marking pattern that is arranged to provide eye tilt information and is used in conjunction with other eyetracker components such as, for example, beam splitters, a patient fixation light, a surgical microscope with alignment marks on the oculars, a turning mirror, a video camera, a photodiode array sensor, an eyetracker camera (if the video camera is not used for the same), an electronic video frame grabber, and head holding means such as a cervical pillow. With information provided by the eyetracker system, a laser system computer and related detection software enables the present invention to capture process and establish the initial corresponding reference coordinates for the eye and any subsequent shifts of the eye along an X-Y plane and/or eye tilts about the eye's normal axis.

Active eyetracker operation is facilitated under the present invention in the utilization of two main contrast landmarks of the eye in the context of both reference marking and in analyzing the position of the eye both with respect to X-Y plane shifts and normal axis eye tilts. The two landmarks include, for example, the contour of the iris and the pupil. The iris provides an advantageous location for reflecting the reference marking pattern of the marking means while the pupil center point provides a convenient reference point for comparison purposes with respect to those reference markings for determining whether the eye is tilted. This information is used, for example, in conjunction with reference to the reticula marks on the oculars of the surgeon microscope and the typically corresponding eyetracker camera's centration marks wherein movement of the eye can be broken down both from the standpoint of eye tilt angle and eye shift along the X-Y plane. Preferably the non-invasive reference marking device utilizes the cornea refraction and iris reflectivity in association with a plurality of auxiliary satellite markers (e.g., illumination lights, ring illumination lights and/or laser pointer lights) which can be used for the initial centration and alignment of the eyetracker and the targeted eye and for tracking of movement of the eye after the initial reference is taken.

Eyetracker detection and correction is based on, comparisons between, for example, initial and subsequent X and Y reference coordinate values for changes associated with the referencing technique of the present information which provides information both as to any eye shift and any eye tilt. For example, by comparing with the laser system computer the digital position information provided with respect to the initial captured image against a later image capture relative to any changes in the reference position parameters providing the eye tilt and shift information, accurate tracking of eye tilt and shift is made possible under the present invention. The eye tilt and shift analysis information is also used under the present invention to compensate the laser beam delivery system to conform to such changes in eye position.

In a preferred embodiment, the eye tilt movements are detected as centration variations of, for example, a central point in the pupil, within surrounding concentrically arranged reference marking points and/or one or more concentric marker rings generated by the non-invasive reference marker means. The reference marker positioning can be mapped and converted to digital position information in accordance with the software associated with the eyetracker camera being utilized for displacement by the computer processor. Data relating to the detected reference pattern provided by the reference marking means through the cornea (and preferably projected on to the iris) and any concentricity variations relative to the center of the pupil center, for instance, with respect to the reference pattern are processed by the computer and the detection software to detect any angle tilt in the normal axis of the eye. The same reference marking means can also be used to detect non-tilt shifts in the eye.

The present invention is also directed at providing a laser delivery system that utilizes the active eyetracker's shift and tilt information in providing laser beam delivery commands that corrects for any detected shift and/or tilt. All the information provided by the eyetracker system is properly processed via the computer and the detection software to generate compensations for these eye movements via the excimer laser delivery system before the delivery of the next individual excimer laser pulse to the patient cornea to precisely place and deliver every laser pulse in the exact location required by the programmed surgery.

The present invention can also be used in conjunction with conventional laser systems to take advantage of the ability of the present invention to determine eye tilt and differentiate the same from a generally non-tilt shift or a combination. For example, this information is of high importance in the initial video frame reference capture and can also be used to determine if the eye has moved into an unacceptable tilt warranting a no-shot signal to the laser system (e.g. an extreme tilt might warrant a no-shot signal despite the fact that the pupils shift on the X-Y plane falls within acceptable shift parameters for a shot by the laser) The present invention is, however, more preferably used in conjunction with a laser system capable of properly following along with eye tilting to provide essentially equal energy application across the desired laser beam contact area(s).

The present invention further features a laser delivery system that includes an optical assembly which is capable of accommodating movements in the eye and particularly eye tilt variations. In one embodiment of the invention, the optical assembly includes means for delivering an excimer beam along a path coincident (or parallel in certain special situations as in a presbyopic off-center ablation pattern center or a surgeon's override) to a tilted eye's designated tilt reference axis (e.g., the optical axis of the eye). This embodiment preferably features a first optical path directing device (preferably fixed) that directs the laser beam to a second optical path directing device preferably in the form of an adjustable scan mirror which delivers the beam and then to a third optical path device that includes a curved, ellipsoidal mirror. The scan mirror is positioned at the focal point of the ellipsoidal mirror (preferably a one quarter section of an ellipsoid) with the combination of the ellipsoidal mirror and scan mirror being oriented so as to cover the entire surgical ablation area common for eye surgery. The first directing device is helpful to enable the proper positioning of the laser beam onto the adjustable scan mirror located at one of the focal points of the ellipsoidal mirror. The ellipsoidal mirror will direct all incoming light rays toward a second focal point of the ellipsoidal mirror which coincides with the base point of the cornea's radius. The ellipsoidal mirror is also dimensioned and arranged to cover the entire cone area of tilt (with the cone's central axis coinciding with a non-tilt orientation of the eye which typically is the reference setting for the laser beam delivery system and the base of the cone preferably being along the iris plane). The ellipsoidal mirror associated with this laser delivery system thus negates the tilt of the eye in beam delivery so as to require only a determination as to where, on an X-Y plane, the laser beam axis should be directed. That is, under the present invention, a particular point on the curved mirror corresponds to a particular point on the cone base of tilt possibilities and is at angle directed at the cornea's focal point. Accordingly, the eyetracking system merely needs to assign an X-Y plane point to the laser delivery system's control to have the beam traveling off the curved mirror coincide with any eyetracker determined tilt orientation of the eye. Thus, for example, a large beam spot application having a predetermined pattern (based on, for instance, the use of a mask in line with the beam such as a mechanical iris device, a molded plastic material beam absorption mask insert, or an active pixel based mask as described below, etc.) can be applied with greater accuracy in a tilted eye situation so as to achieve greater conformity with the intended and resultant final ablation in the eye.

Another laser delivery system that can take advantage of the additional, accurate eye tilt information is an active mask system such as those described in co-pending U.S. Ser. Nos. 09/598,226 and 09/598,227 each filed on Jun. 21, 2000. These active mask systems are pixel based systems that can readily turn off or on desired pixels to achieve desired resultant ablation volume patterns in the eye. Thus, if a tilt determination is made, adjustments can be made in the pixel pattern presented to the laser beam to compensate for any energy variation that would arise if the beam was presented to an eye that is tilted. Thus, through coordination of the eyetracker system with the pixel pattern setting system described in the above application energy variation adjustments can be made in the pixels prior to the next laser beam pulse. A preferred embodiment features a pixel based mask like those described above which can provide different levels of transmissivity amongst the pixels to apply an energy pattern directed at negating any eye tilt.

The present invention is also directed at an initial patient positioning system that has an automated feature with a preferred embodiment having the eyetracker system utilize the reference markers in conjunction with a focusing control of an eye viewing device such as the eyetracker camera or some other camera or eye image viewing means including a surgical view video camera or the surgeons microscope. Through a series of sequential focusing steps with respect to, for example, the reference pattern of the present inventions reference marking means in coordination with adjustment in the patient bed movement system, the laser system can properly position the patient's eye at a desired reference setting close to or at the proper laser beam start position. This is accomplished by first providing an input that will enable the bed to automatically move to a pre-established setting (e.g., a memorized setting from an earlier surgical procedure) that brings the patient's head within a camera's general view field. The surgeon also inputs an indication as to whether the right eye or left eye is being treated (an OD or OS command). Once the bed has moved to the general field location and the OD or OS information provided, the eyetracker system, in conjunction with the focusing means of the cornea and the bed adjustment means, carries out a fully automated sequence wherein, through a loop sequence of focus determinations and bed adjustments (and/or tilt pillow head holding means), the eye can be adjusted to at (or essentially at) the laser's reference settings.

In a preferred embodiment of the invention the reference marking means utilize visible light beams that are strategically positioned for the purposes of reference information, and also to provide the lighting required by the eyetracker camera and microscope for proper functioning. Accordingly, the present invention provides the refractive surgeon with a very precise eyetracker that utilizes the reference marker lights as coaxial and/or auxiliary illumination lights for illuminating the operating field without the limitations and inconvenience seen in the previous infrared side illumination systems like infrared power changes, infrared contamination and infrared video noise generated by the activations and control of the microscope illumination and auxiliary lights when used by the surgeon during the execution of a refractive surgery.

Also, contrary to prior art systems that restrict illumination, the present invention is designed so as to encourage and even suggest with this system the use of excess illumination to enhance the detail view of the surgery for the surgeon and to greater the color contrast for the peak video detection of the different video eye targets comprised of limbo, iris, pupil and the reference lights.

The contrast and power balance is, for example, controlled and balanced under the present invention via an electronic automatic gain control (AGC) feed back in the camera to maintain the same working threshold regardless of the illumination conditions.

The present invention thus further provides a surgeon with an active eyetracker system able to detect changes not only for the X and Y plane as in the prior art, but also changes in the tilt of the eye and make the compensations via the ablation delivery system. Also, as discussed above, the present invention also features laser delivery systems that can take advantage of the tilt determination capability of the eyetracking system of the present invention.

BRIEF DESCRIPTION OF THE PREFERRED EMBODIMENTS OF THE INVENTION

FIGS. 3B to 6B provide a respective side elevational view of the eye for each of FIGS. 3A to 6A.

FIGS. 3C to 6C illustrated schematically the relative relationship of the pupil center and the reference point marks for each of FIGS. 3A to 6A.

FIG. 7A shows the application of a laser beam subjected to an astigmatic correction pattern landing on an eye in a normal setting and two different tilt orientations.

FIG. 7B shows the energy density levels for the applied laser beam and eye orientations in FIG. 7A.

Figure 8:
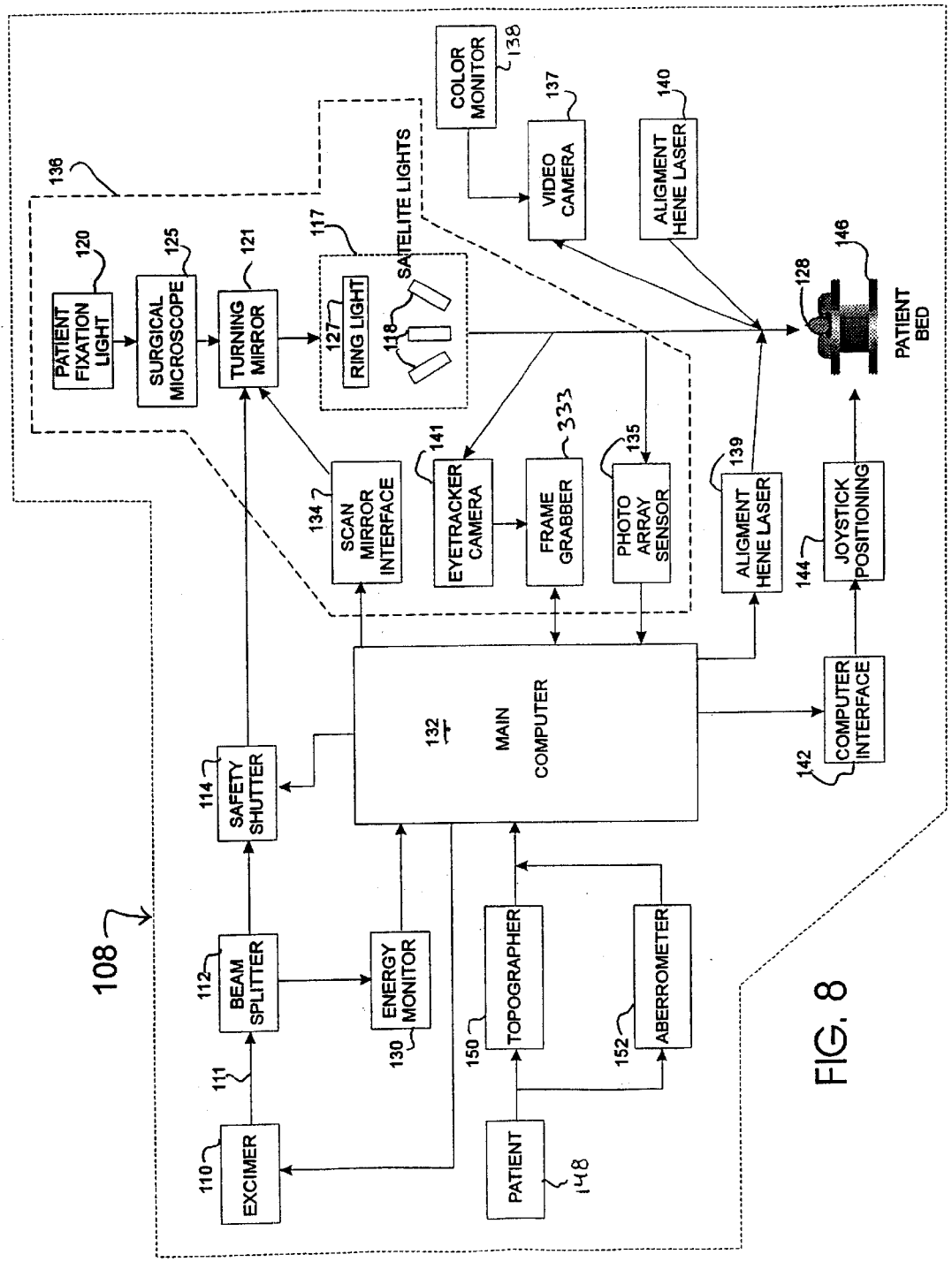

FIG. 8 shows a block diagram of the laser system of one preferred embodiment of the invention featuring the present invention's improved eyetracking system working in conjunction with a conventional laser delivery system.

Figure 9:
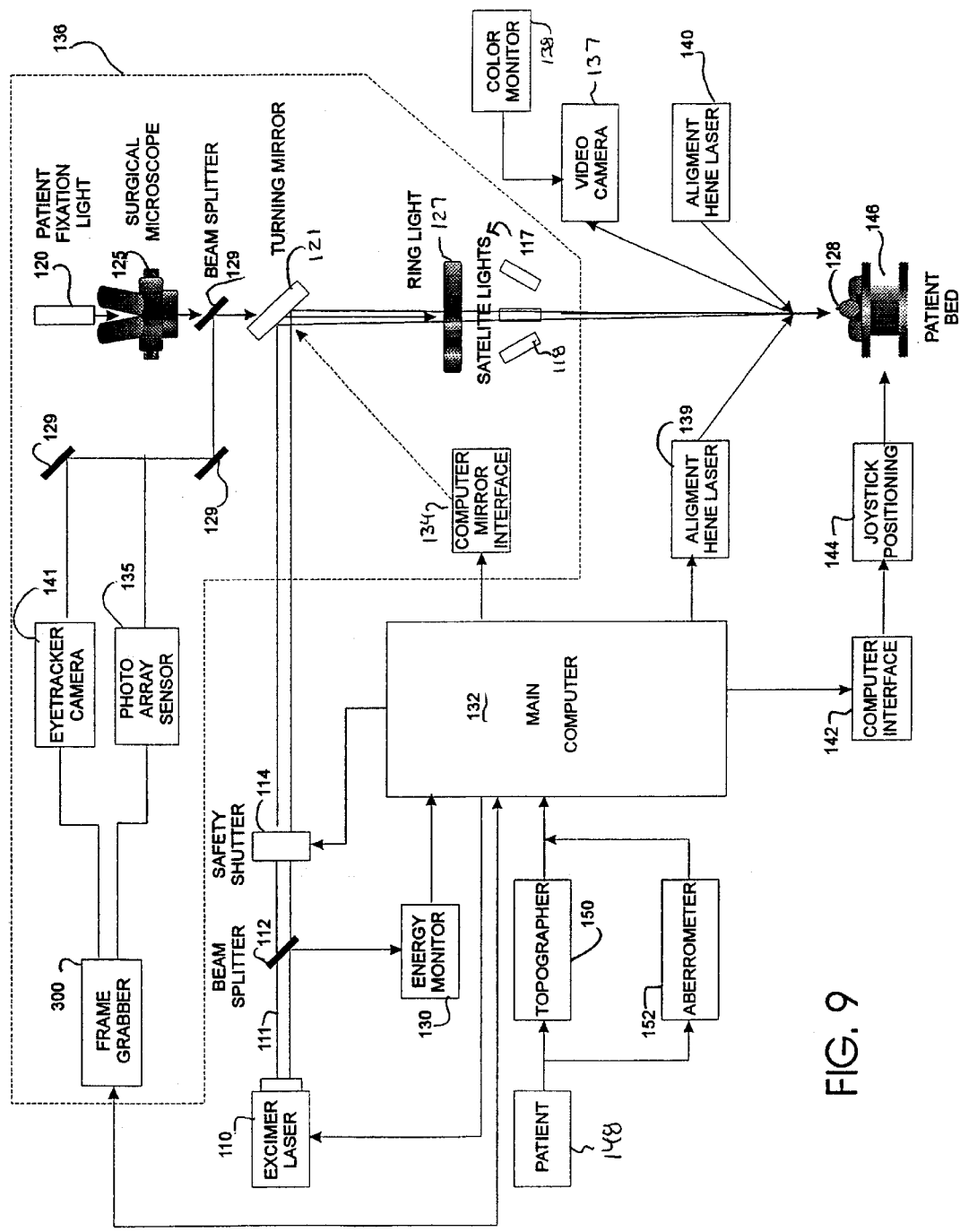

FIG. 9 provides a schematic physical presentation of that which is shown in FIG. 8.

Figure 10:
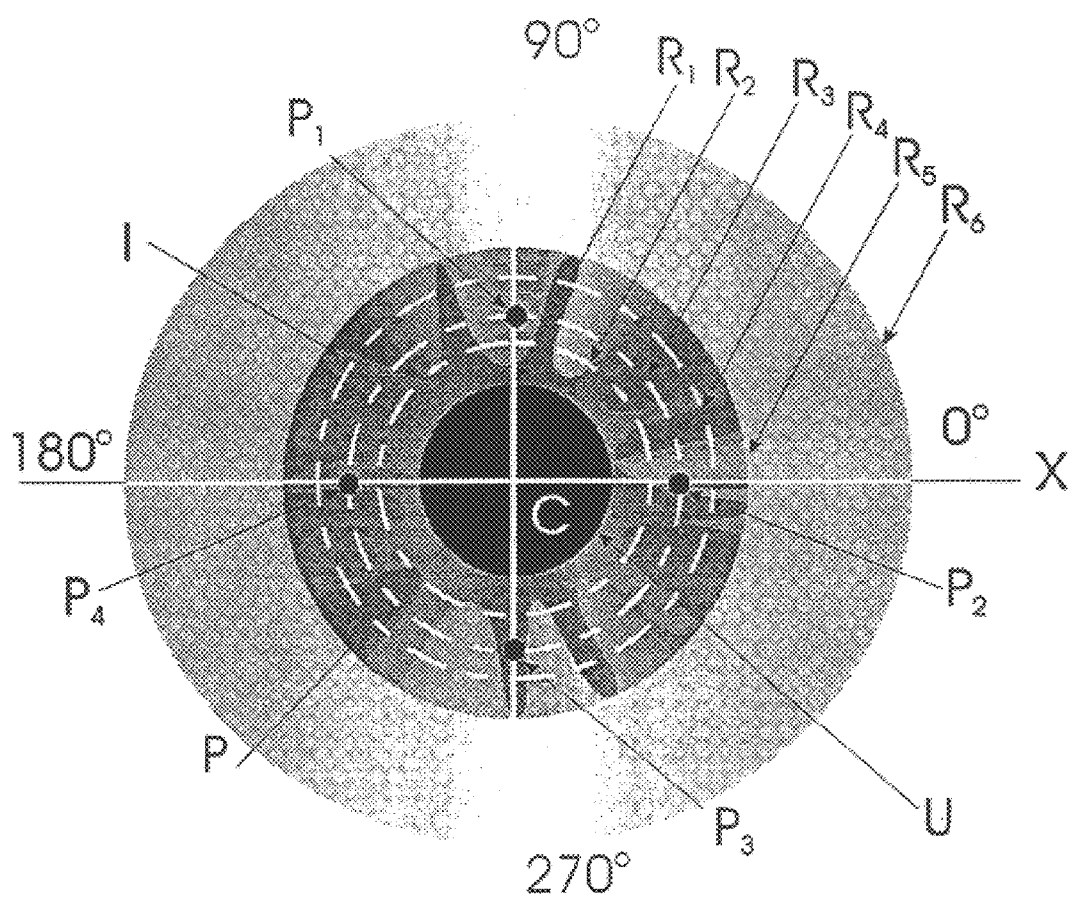

FIG. 10 shows an iris depiction and some preferred locations for the reference points and/or rings of the reference marking means of the present invention.

Figure 10A:
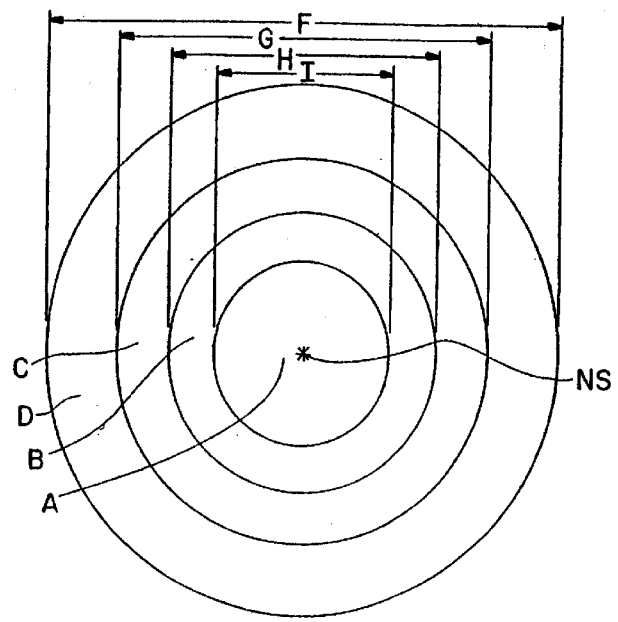

FIG. 10A shows an ablation volume zone framework for use in presbyopic laser surgery.

Figure 10B:
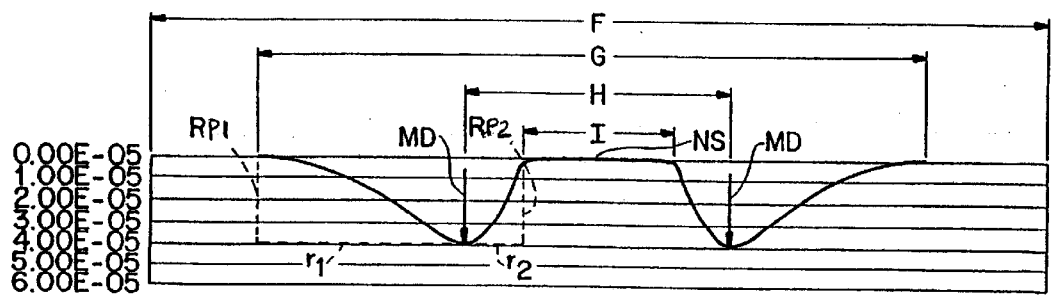

FIG. 10B illustrates an ablation pattern which utilizes the framework of FIG. 10A in providing an ablation pattern highly effective in removing the presbyopic effect on an eye.

Figure 10C:
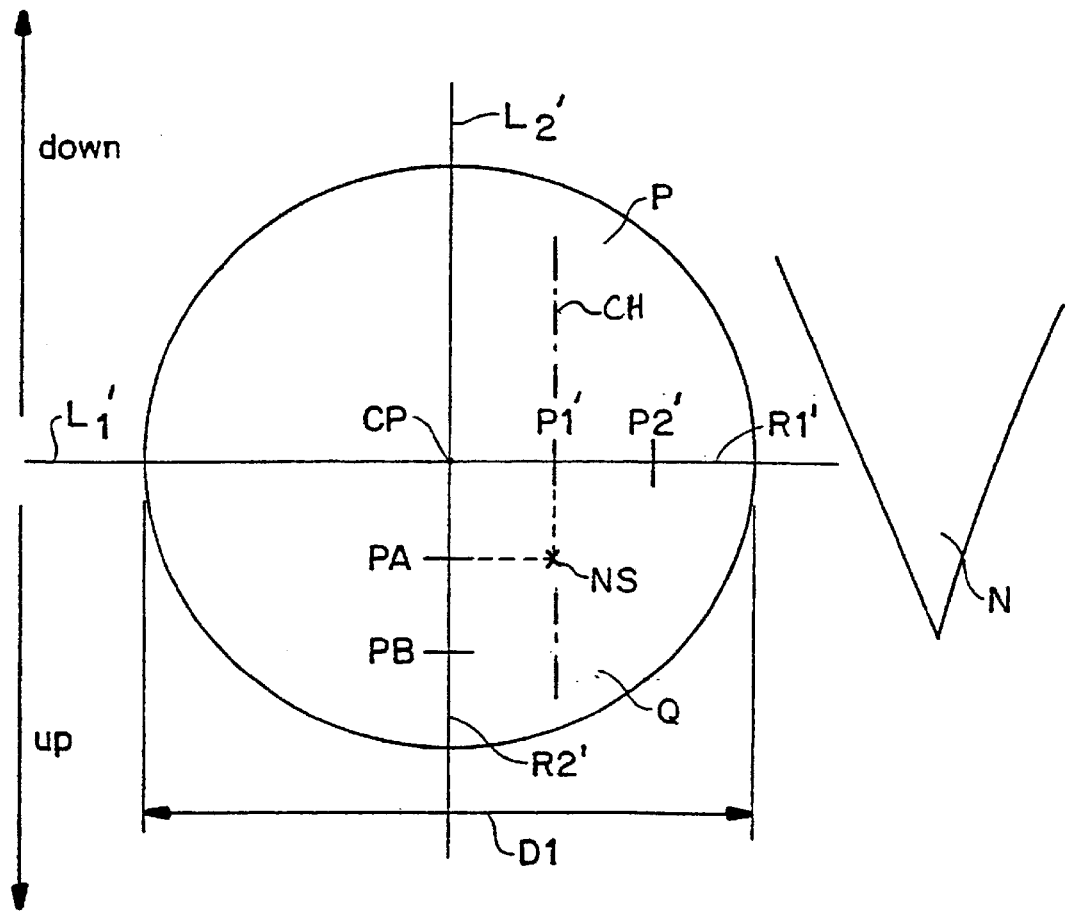

FIG. 10C provides a schematic view for determining the preferred center point for the zone of FIG. 10A in the pupil of an eye.

FIGS. 11A–11D show various positions of an eye and how the reference point markers appear on those eyes.

Figure 12A:
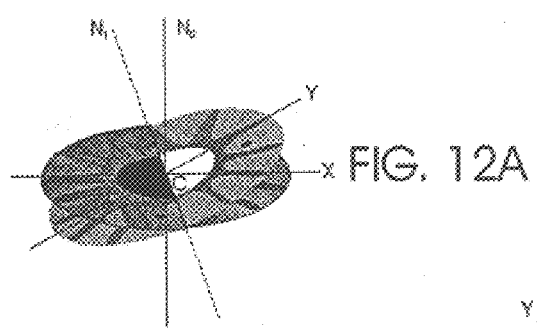

FIG. 12A illustrates an iris in both an initial non-tilt setting and a tilted setting.

Figures 12B, 12C:
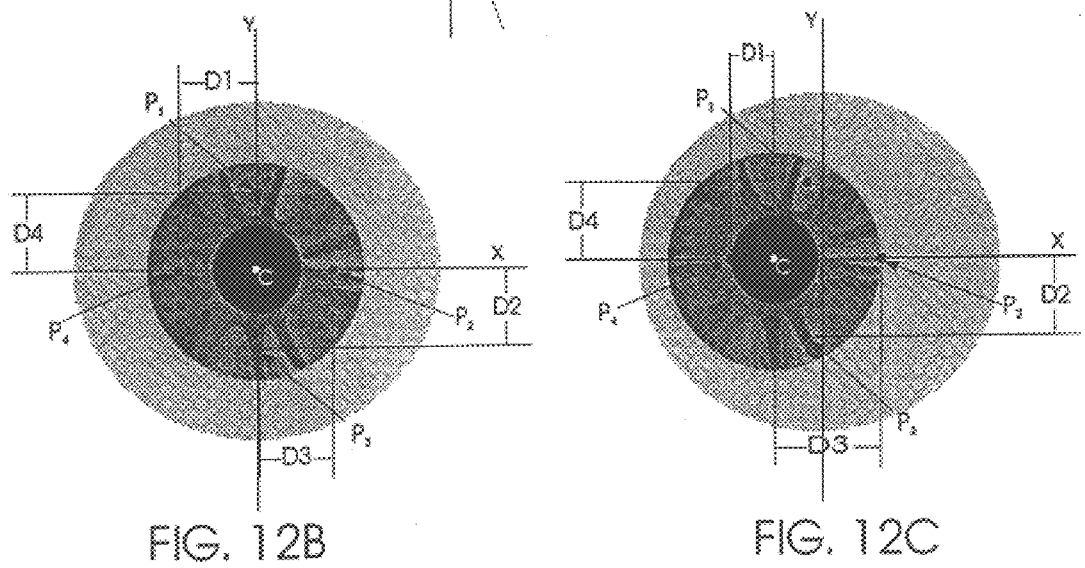

FIGS. 12B and 12C show, respectively, the relative position of the reference point markers and pupil for the iris positions shown in FIG. 12A.

Figure 12D:
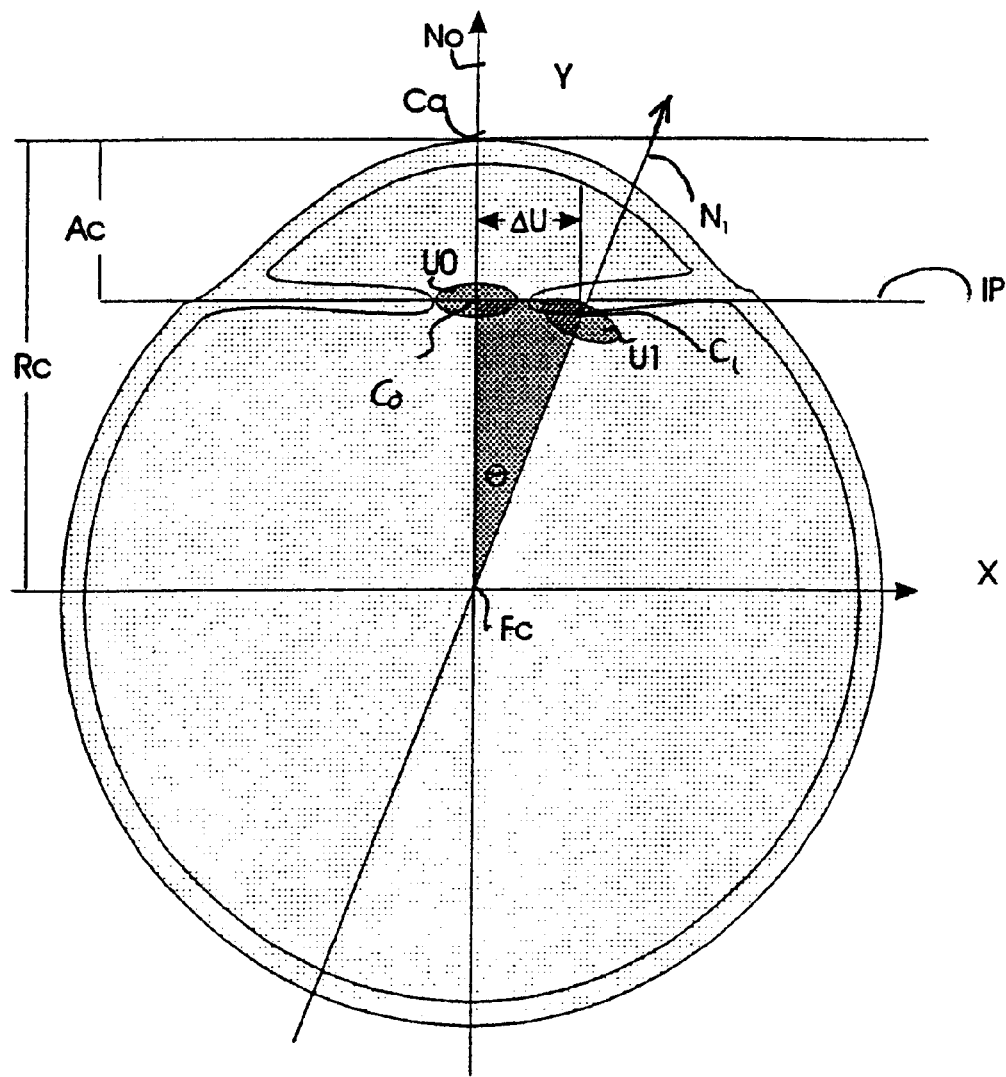

FIG. 12D provides a cross sectional view of an eye both with the pupil in a normal (non-tilt) position and in a tilt position.

Figure 12E:
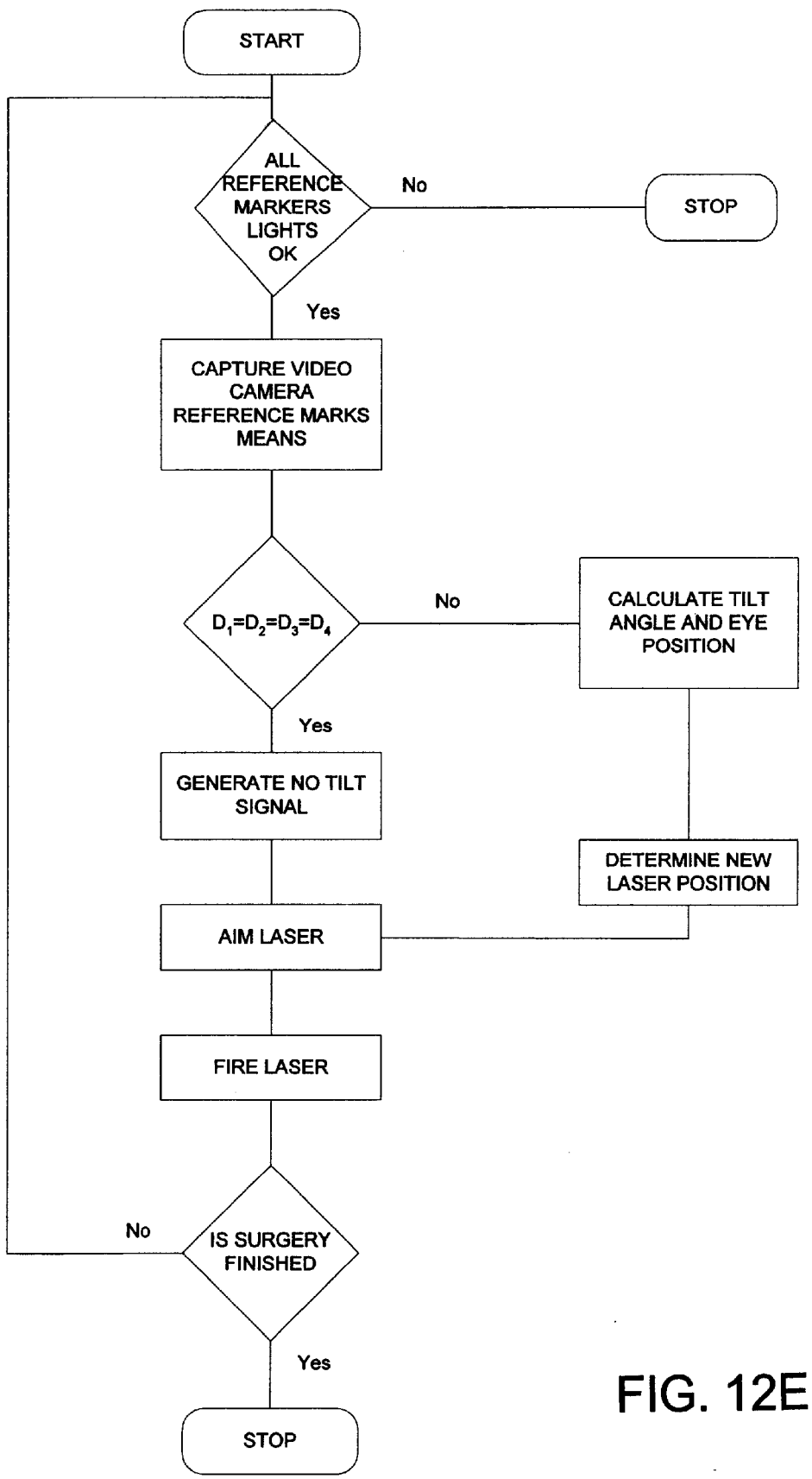

FIG. 12E provides a flow chart for a routine involving the markers shown in FIGS. 12B and 12C.

Figure 13:
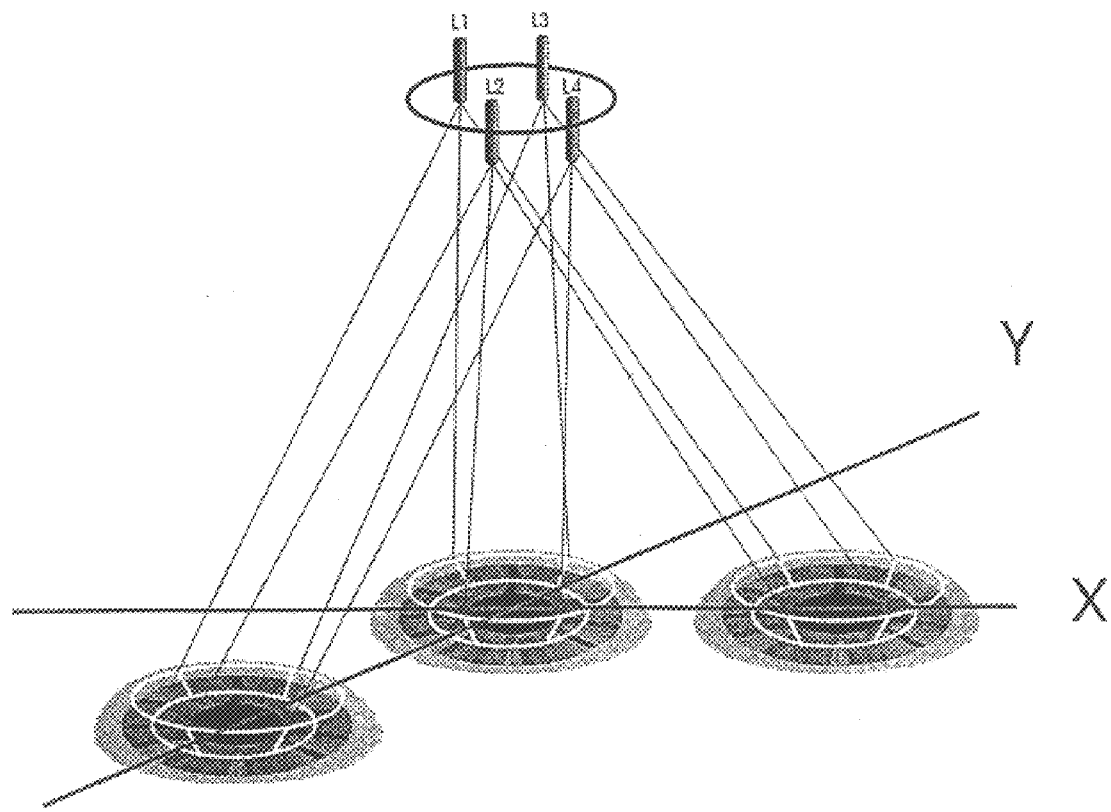

FIG. 13 illustrates a group of reference point markers projecting on to the iris area of an eye in three different shift settings on an X-Y plane.

Figure 13A:
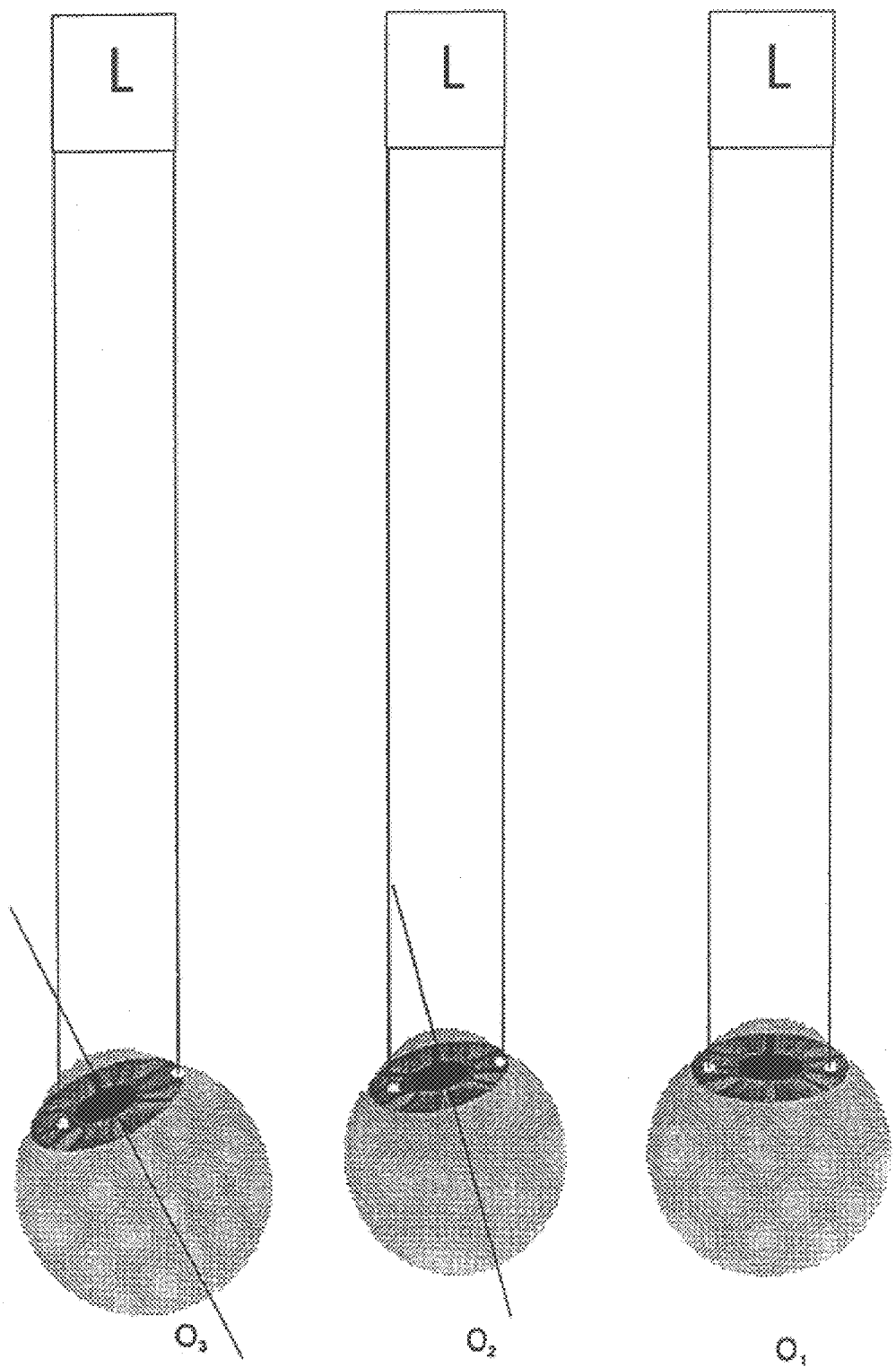
Figure 14A:
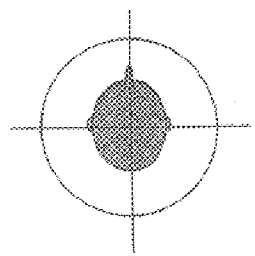
Figure 14B:
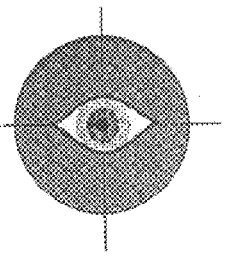
Figure 14C:
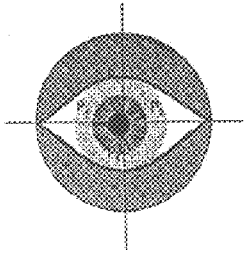
Figure 14D:
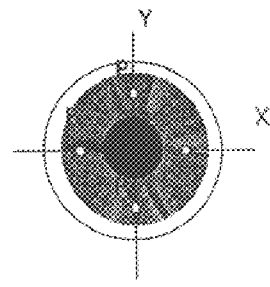

FIG. 13A illustrates a pair of pointer mark applications on a common axis of an eye and the relative movement of those points with respect to the pupil in going from a no tilt position to two different degrees of tilt.

FIGS. 14A to 14D illustrate the appearance seen through a surgeon's microscope during the process of bringing a patient's eye into an initial data capture setting.

FIGS. 15A to 15D illustrate the appearance seen through a camera lens during the process of bringing a patient's eye into an initial data capture setting through use of focus level analysis between patient support shifts.

FIGS. 16A to 16F illustrate a tilted eye as seen though a video camera monitor and the reference marker point appearance therein following different software filter manipulation of the stored digital image.

Figure 17:
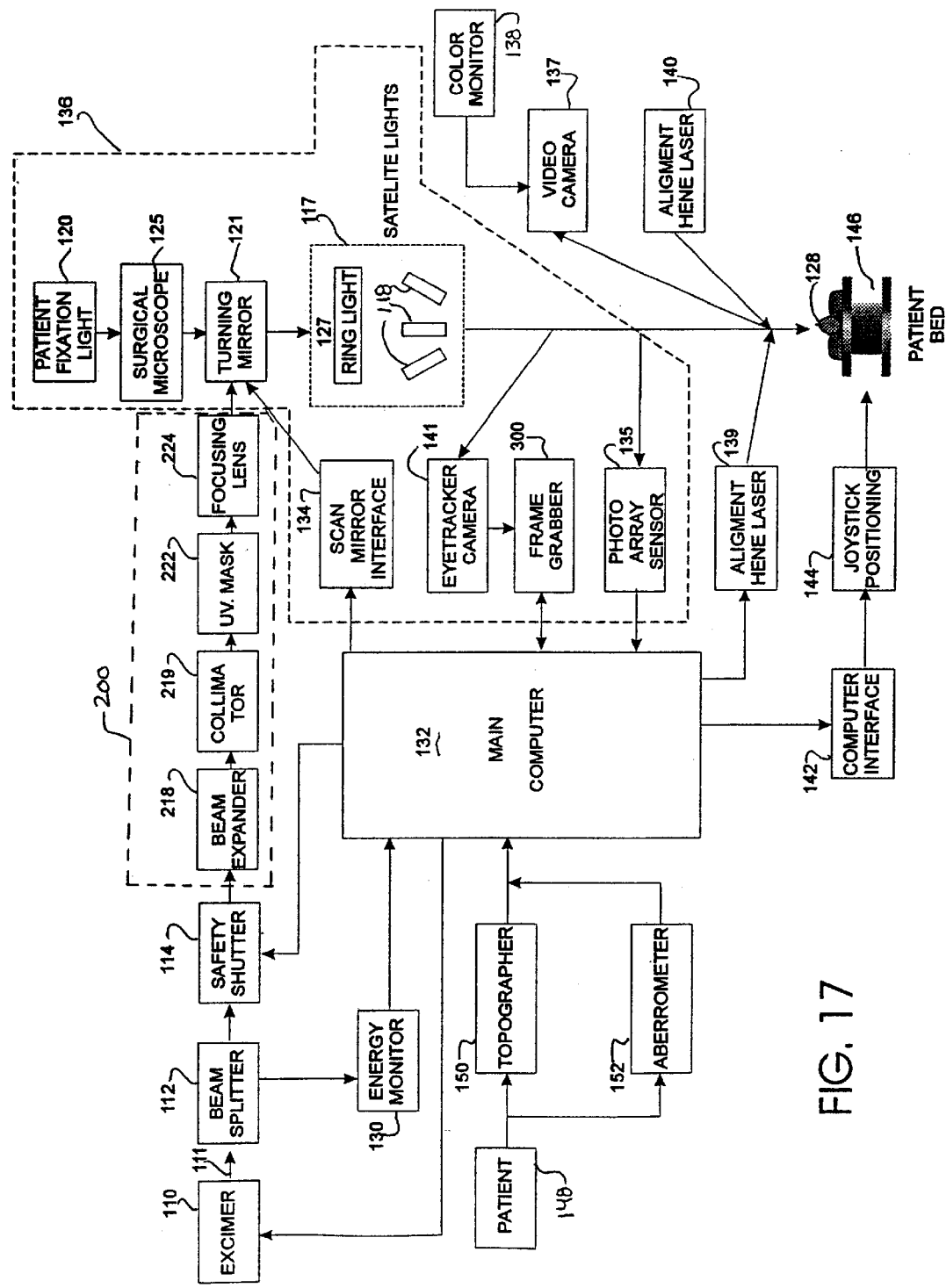

FIG. 17 provides a view similar to that of FIG. 8 with the addition of an active mask in the optical path of the laser upstream of the turning mirror.

Figure 18:
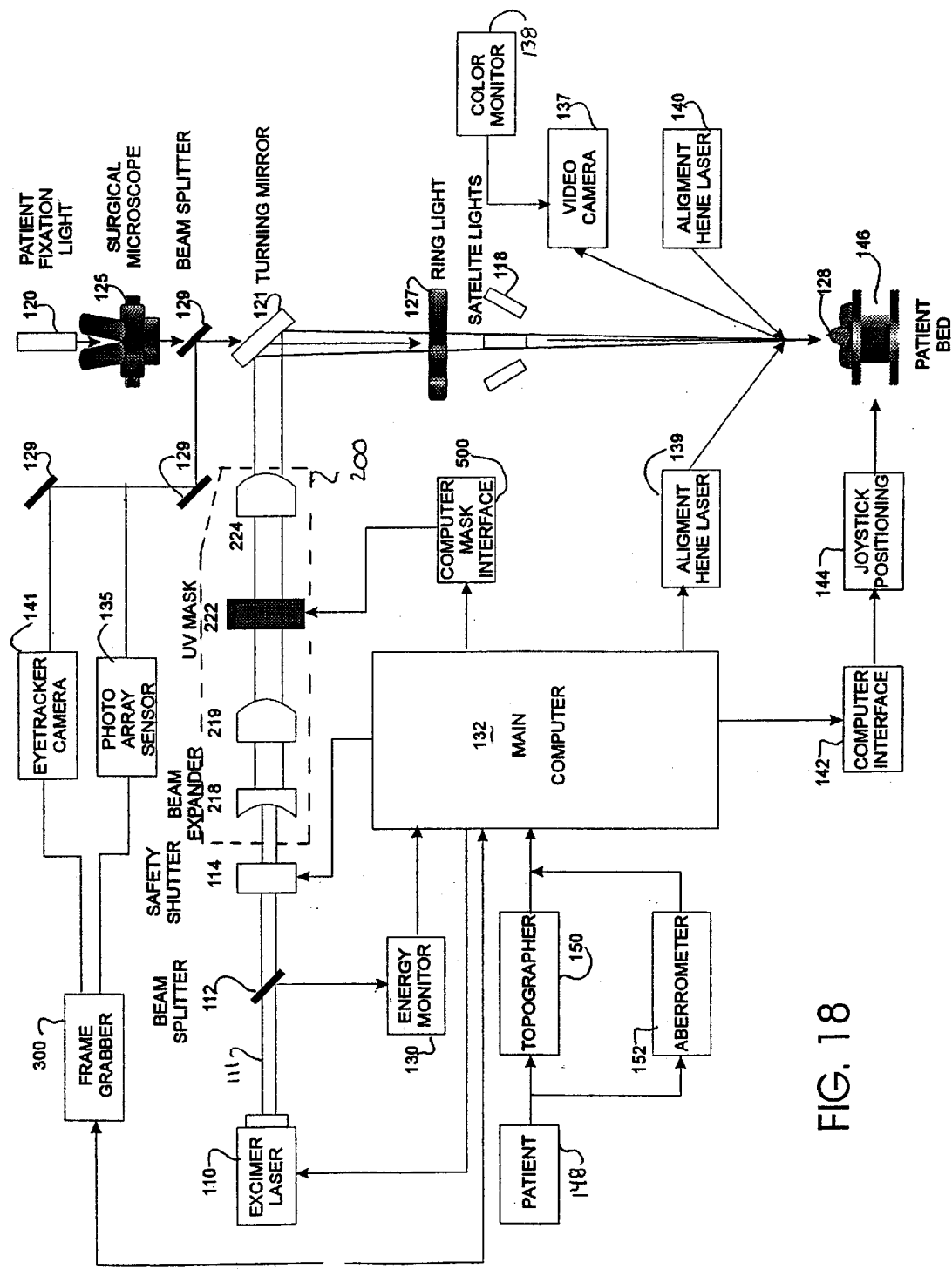

FIG. 18 provides a schematic physical presentation of that which is shown in FIG. 17.

FIG. 19A provides a schematic view of one embodiment of the active mask shown in FIG. 17.

FIG. 19B provides an expanded view of the circled portion in FIG. 19A.

Figure 19C:
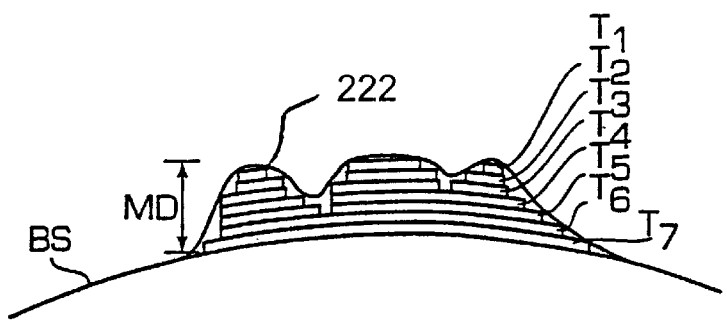

FIG. 19C illustrates a total volumetric ablation pattern producible by the mask in FIG. 19A.

Figure 19D:
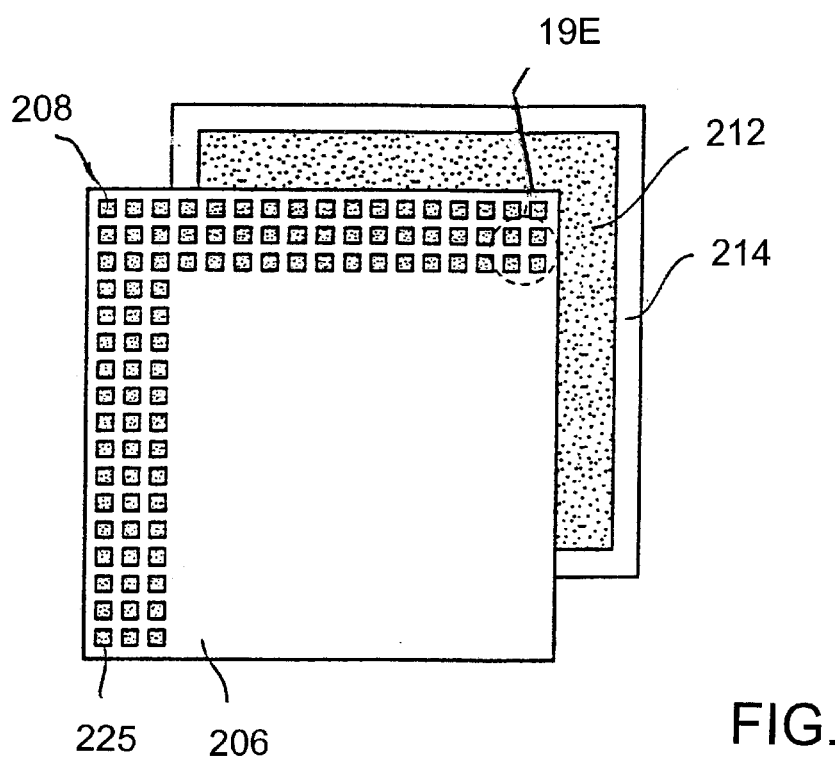
Figure 19E:
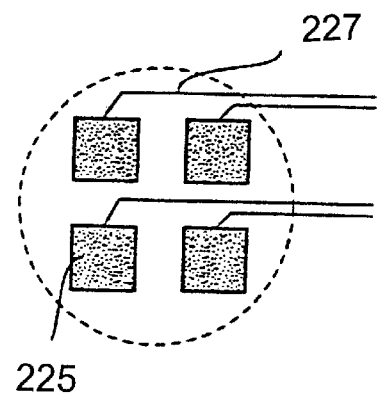

FIGS. 19D and 19E provide an illustration of the electrode components of the active mask in FIG. 19A which provides individual, controllable pixels.

FIGS. 20A, 20B and 20C provide schematic presentations of an electrochromic, pixel based active mask.

Figure 21A:
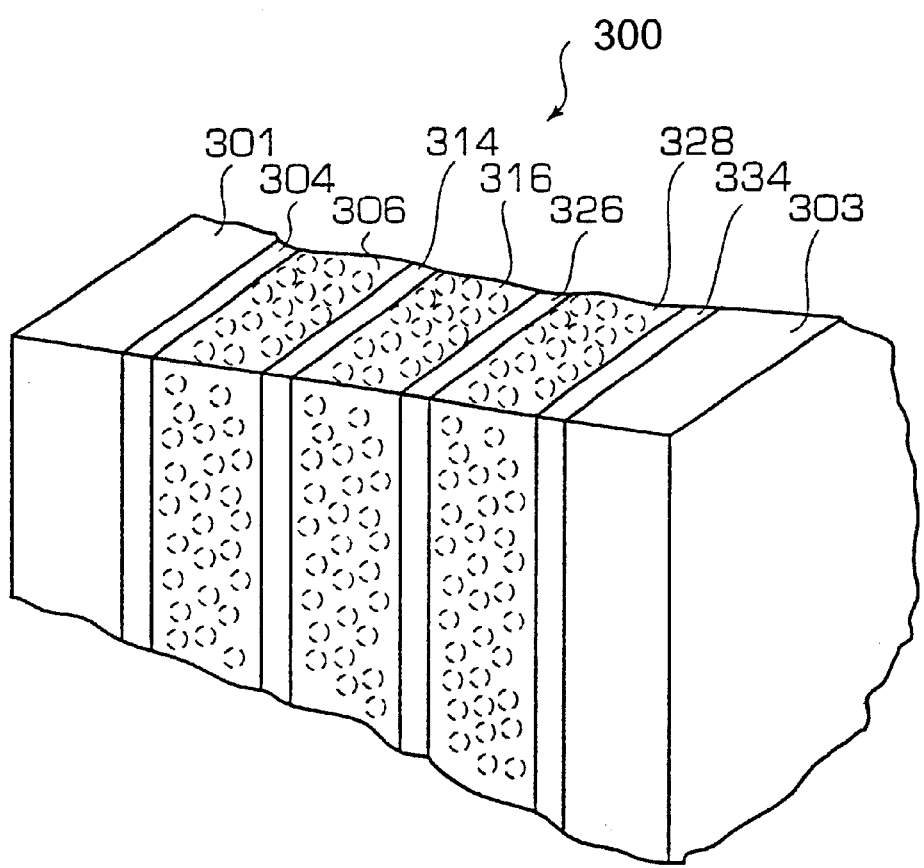

FIG. 21A illustrates a section of an active mask based on a plurality of bubble dispersed liquid crystal pixel cells.

Figure 21C:
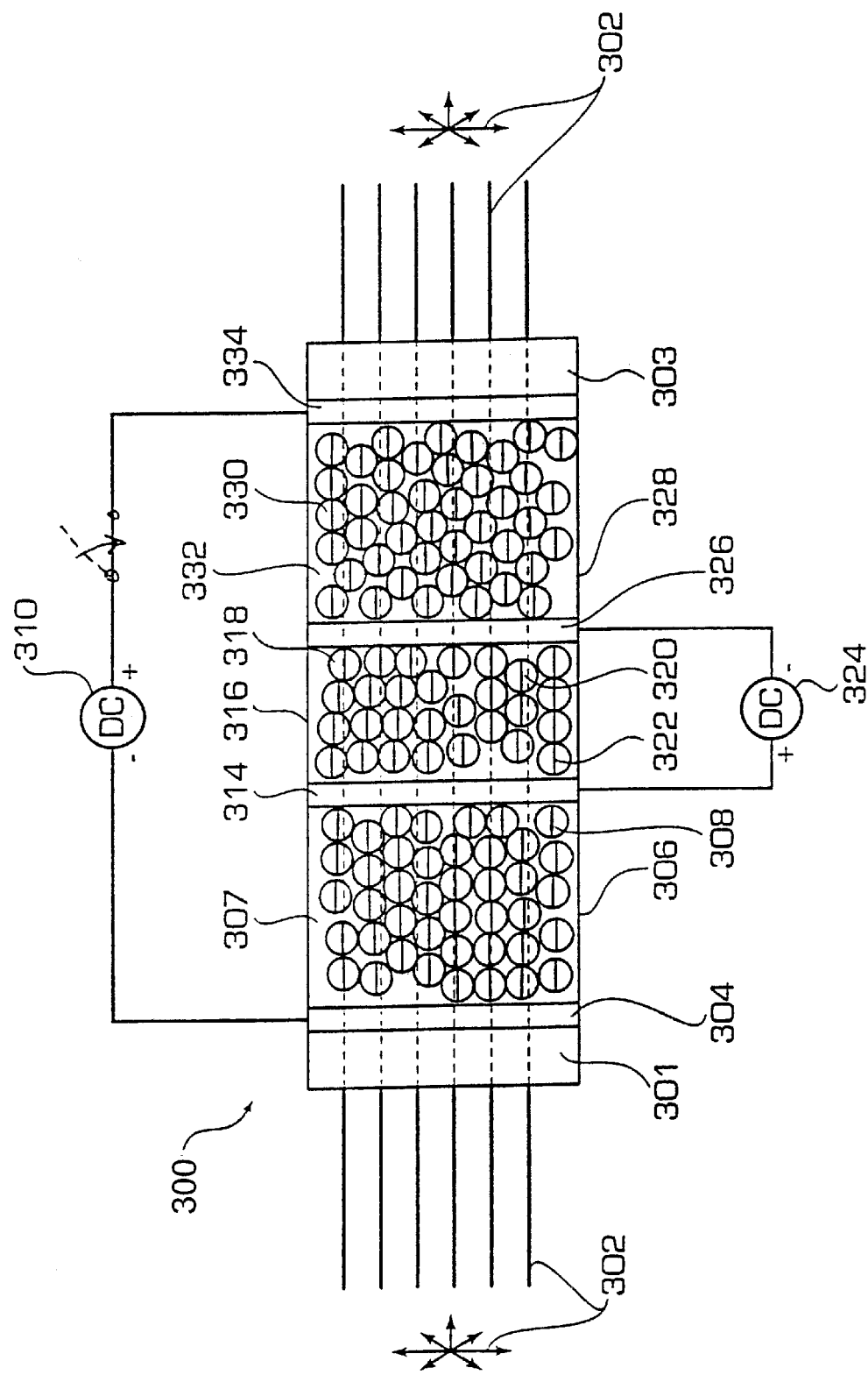

FIGS. 21B and 21C schematically illustrate the pixels for the mask in FIG. 21A in blocking and full non-blocking states.

Figure 22:
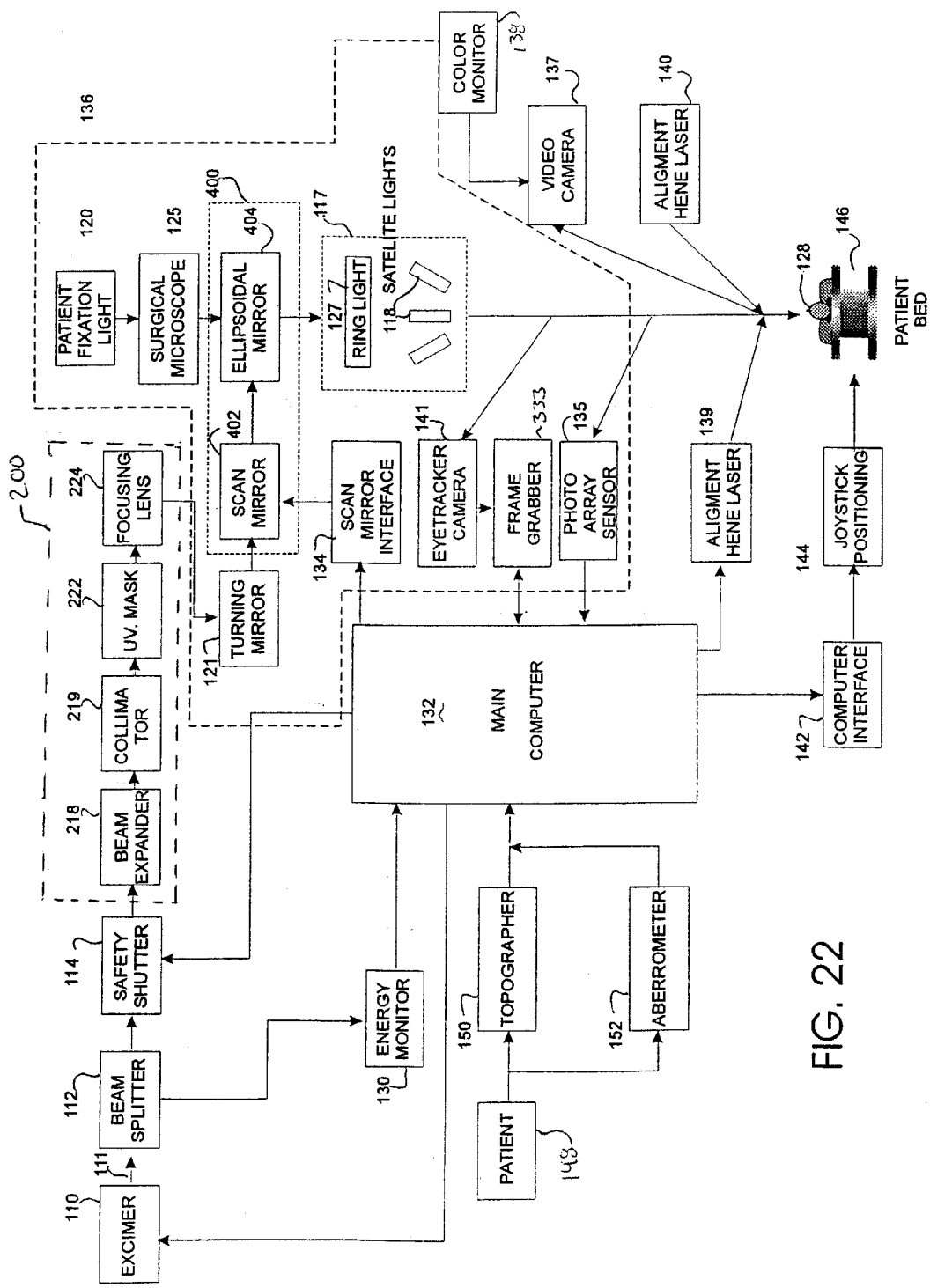

FIG. 22 shows a view similar to that of FIG. 8 except for having tilt accommodation laser delivery means featuring an ellipsoidal mirror in line with the optical path.

Figure 23:
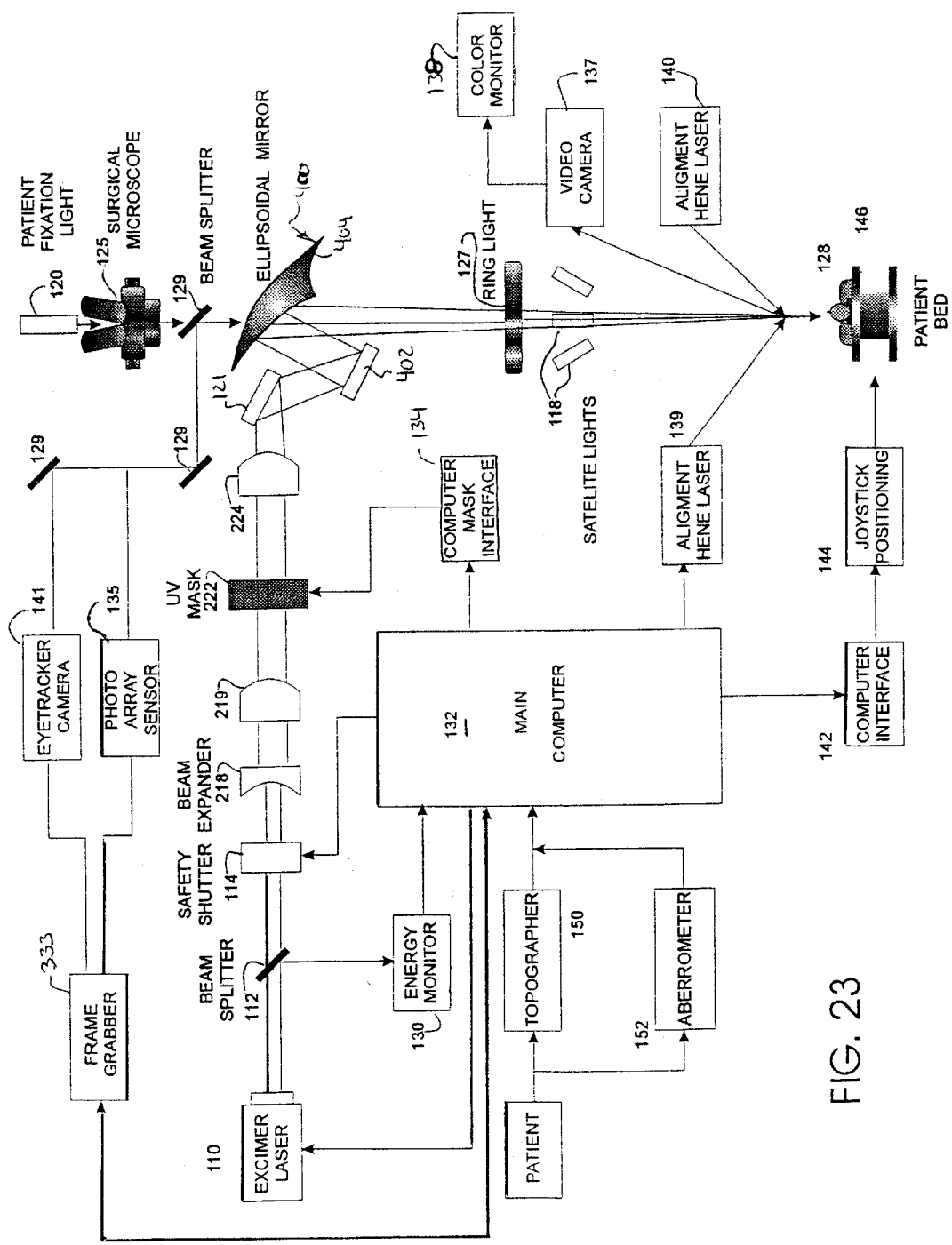

FIG. 23 provides a schematic physical presentation of that which is shown in FIG. 22.

Figure 24:
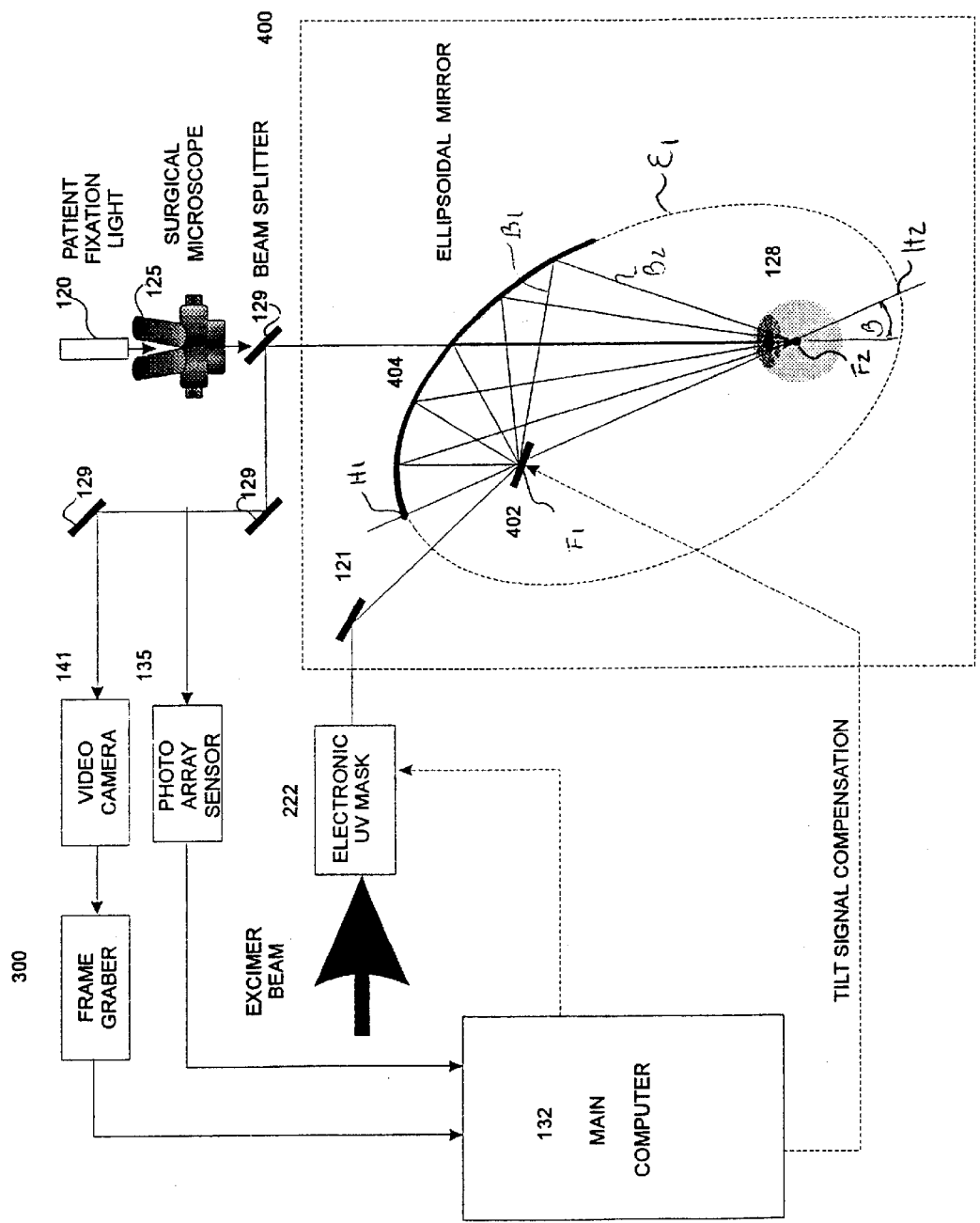

FIG. 24 provides a schematic visual presentation of some of the components of the laser system shown in FIG. 23 with emphasis on the tilt accommodation laser delivery system in conjunction with an eyetracker system.

Figure 25:
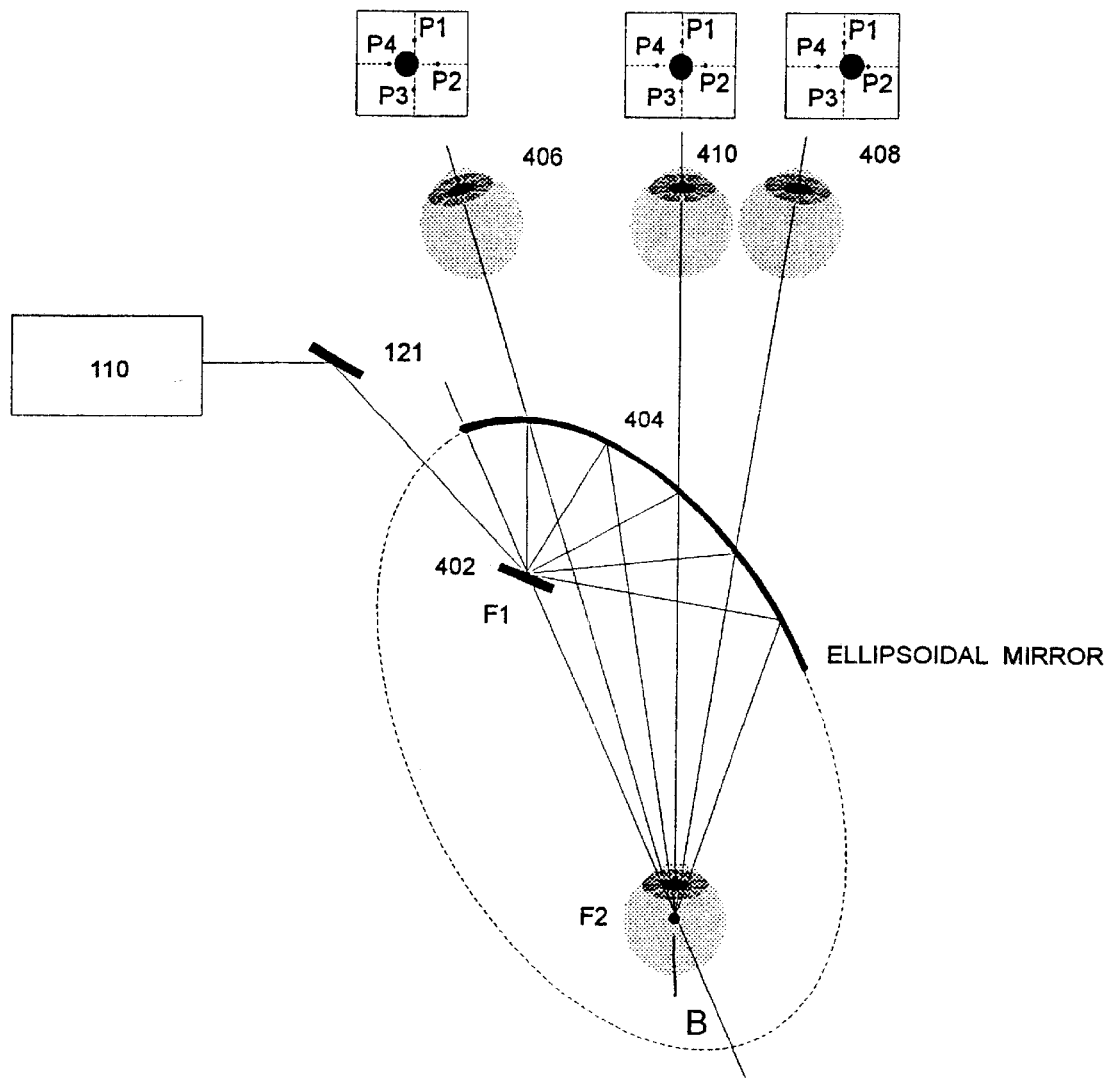

FIG. 25 provides a schematic view illustrating the relationship between the eye tilt reference marker determination and matching adjustments in the tilt accommodation delivery system.

DETAILED DESCRIPTION OF THE PREFERRED EMBODIMENTS OF THE INVENTION

Figure 1:
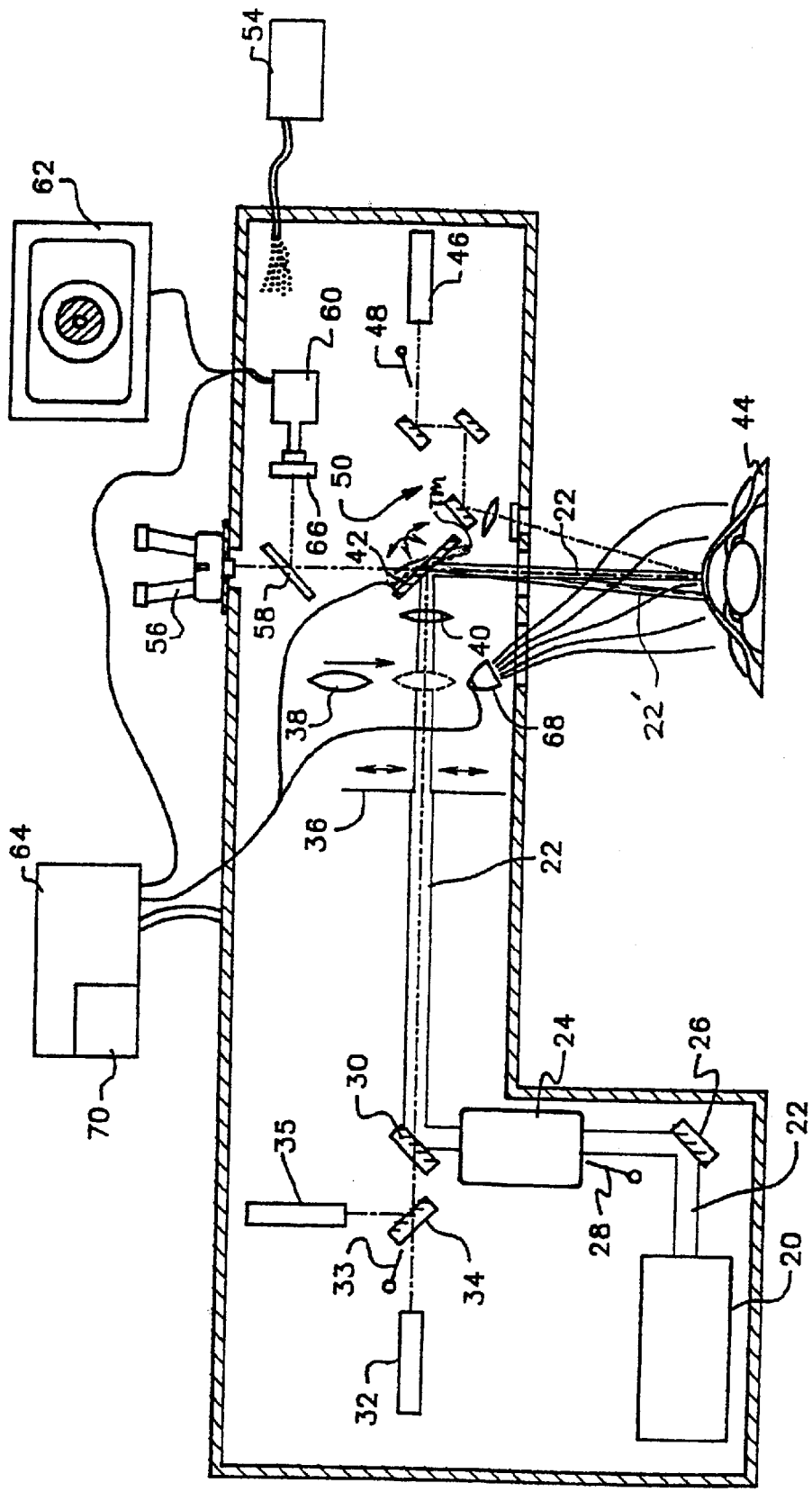
FIG. 1 illustrates a schematic view of a prior art laser delivery system with an infrared based eyetracker system.

To help appreciate the differences between the present invention and the prior art, reference is first made to the prior art laser system illustrated in FIG. 1. FIG. 1 shows prior art laser surgery system 10 as including homogenizer 24 which receives beam 22 from excimer laser 20 after reflection from optics 26. The pulsed beam 22 is then reflected off of optics 30, which also passes an aiming beam from an aiming laser 32. This aiming laser 32 is preferably a low power red 633 nm helium neon laser of less than 1 mW/cm$^2$ of power. The aiming beam from the aiming laser 32 can also be blocked by a shutter 33 and is aligned so that its optical pathway coincides with the pulsed beam 22. The aiming laser 32 provides an aiming beam spot that coincides with the central axis of the laser shot of the pulsed beam 22.

In prior art system of FIG. 1, a registration laser 35 provides a registration beam reflected by optics that is of a wavelength of approximately 950 nm, or near infrared and preferably is low power, less than 1 mW/cm$^2$. This registration beam is used for aiming of the pulsed beam 22.

Following the adjustable diaphragm 36, a focusing lens 40 directs the pulsed beam 22 onto a scanning mirror 42, which then reflects the beam 22 onto a patient's eye 44. The scanning mirror is preferably capable of moving a beam at 5000 mm/sec at the surface of the eye 44. The focusing lens 40 focuses light such that when the eye 44 is at the optimal distance, the pulsed beam 22 is properly focused onto the eye 44. These various lenses and mirrors thus combine to form an optical system providing an excimer beam to the cornea. The optical system creates a laser spot on the cornea, and the spot size is adjustable, along with its location. Location adjustment of the spot is achieved through movement of the scanning mirror as shown in FIG. 1 to achieve different locations of beam ablation on the cornea. For example, mirror 42 is shown in dashed lines adjusted to a new location TM which leads to adjusted beam 22' landing on a different spot on the cornea.

FIG. 1 illustrates focusing laser 46, whose beam can also be blocked by a shutter 48. The focusing laser 46 is preferably a green helium neon laser providing a beam of wavelength of 535 nm and less than 1 mW of power. The beam from the focusing laser 46 travels through optics 50 and impinges on the eye 44 at an angle. The distance of the eye 44 from the eye surgery system 10 is adjusted such that both the beam from the aiming laser 32 and the beam from the focusing laser 46 impinge on the surface of the eye 44 at the same point. A clean gas purge unit 54 ensures that the optics and the beams in the system are free from any floating debris.

A microscope 56 is provided for the physician to observe progress during ablation of the surface of the eye 44 at the same point. This microscope 56 focuses through the scanning mirror 42 and also focuses through a splitting mirror 58. The splitting mirror further provides a view of the eye 44 to a video camera 60. The video camera 60 in this prior art embodiment is sensitive to both visible and infrared light and can include a high resolution S-VHS camera with 400,000 pixels, generating at 50 frames per second. The video camera 60 provides an image output to a capturing video screen 62 and to a control unit 64. The video camera 60 is, for instance, capable of producing a digitized output to provide to the control unit 64.

In the FIG. 1 embodiment, filtering light into the video camera 60 is an infrared filter 66, which only permits infrared light to pass through. This would permit for example, a spot created by the registration beam from the registration laser 35 to be perceived by the video camera 60. Thus, the video camera 60 and infrared filter 66 combine to form an infrared sensitive video unit. Also, in this prior art system of FIG. 1, the eye 44 is illuminated by an infrared light source 68. The control unit 15 shown as containing eyetracking system 70.

U.S. Pat. No. 5,620,436, describes an eyetracking system like that represented by 70 in FIG. 1 as being a Chiron Vision Technolas, which runs on one Transputer™ manufactured by INMOS Limited used in conjunction with a Transputer Frame Grabber™ manufactured by Parsytech, GmbH. The eyetracking system 70 preferably receives the digitized output from the video camera 60 and then provides coordinates of the center of the eye on that video image relative to a preset origin. The eyetracking system 70 provides coordinates of an infrared spot on the eye 44 created by the registration laser 35. These coordinates are then used by the ablation profile software in the control unit 64 to aim the scanning mirror 42 for the next shot from the excimer laser 20.

In the prior art system in U.S. Pat. No. 5,620,436 the eyetracking system 70 provides the coordinates of a central point, or origin 72 (shown schematically in prior art FIG. 2 of this application), relative to the eye treatment area 71 based on the method of operation the eyetracking system 70 uses. For example, if an eyetracking system according to U.S. Pat. No. 4,848,340 to Bille were used, ablated reference marks would be ablated in the eye to provide an origin in the eye. Similarly, if an eyetracking system according to the Sklar patent were used, the origin 72 would be located using topographical data developed based on a projected Ronchi grating on the eye which is coupled with a stored reference Ronchi grating with reliance placed on the so called Moire fringes resulting from the combination.

The ablation profile software running in the control unit 64 in the prior art system shown in FIG. 1 calculates the coordinates relative to the origin 72 of a desired target point 74, which denotes the center of the next desired excimer pulse on the eye 44 from the excimer laser 20. Having received the absolute coordinates of where the origin 72 is located on the video image from the eyetracking system 70, the ablation profile software then attempts to determine the absolute coordinates of the target point 74.

Figure 2:
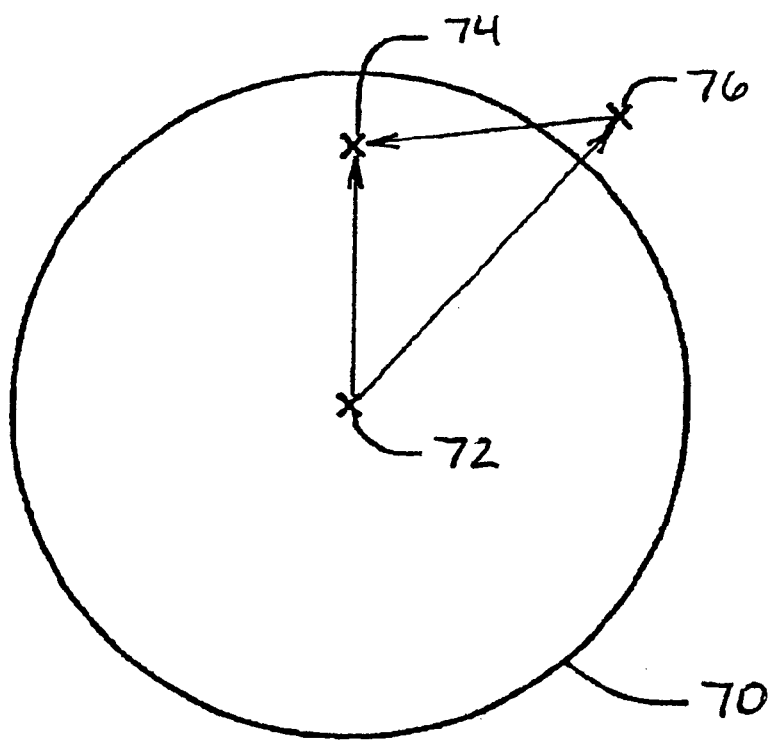
FIG. 2 shows a point detection illustration utilized by the eyetracker system in the prior art laser system of FIG. 1.
Figure 3A:
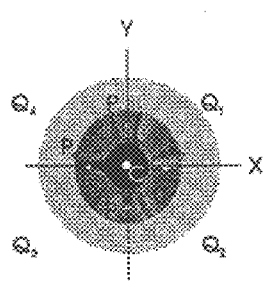
FIG. 3A shows an eye in a non-tilt/non-shift position rendered more apparent through point markers of the present invention.
Figure 4A:
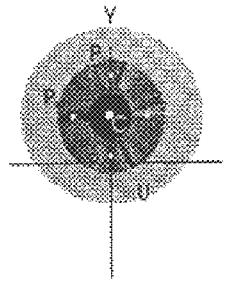
FIGS. 4A and 5A show the eye in FIG. 3A following shifts along the X-Y plane.
Figure 5A:
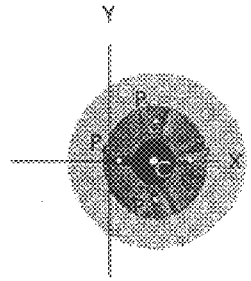

Then, the image from the video camera 60 allows the eyetracking system 70 to locate and provide the coordinates of a registration spot 76 where the registration beam from the registration laser 35 impinges on the eye 44. This registration spot 76 is representative of the center point of where the next pulse from the excimer laser 20 would impinge on the eye if a shot were immediately fired. In FIG. 2, this point is not in alignment with the desired target point 74, perhaps because of intervening movement of the eye 44. The aim of the pulsed beam 22 is therefore corrected in an effort to have the registration spot 76 coincides with the target point 74. This alignment is then again checked, and when within acceptable limits, the excimer laser 20 is fired.

As explained in the background portion of the invention, the prior art system shown in prior art FIGS. 1 and 2 suffers from a variety of drawbacks. For example, the infrared based camera system is easily corrupted by environmental lighting as previously described due to the infrared component of the environmental lights. This prior art system is not suited for determining eye tilt and also is not suited for differentiating between when an eye has shifted on the horizontal X-Y plane and when it has instead only tilted or a combination of the both. The other prior art alternatives described above also suffer from drawbacks such as having to rely on actual ablation of the eye as shown, for example, in the Bille patent, to achieve the reference origin. This not only adds to patient discomfort, but can also lead to undesired adjustment of the topography of the eye and involves extra time consuming steps. Reference origin determination using the above described Ronchi grid overlying is very difficult to establish the desired origin point due to grid interference variations and is highly complex from a calculation standpoint. The additional prior art techniques for establishing a reference origin include the application of a dye pattern directly to the eye or use of physical markers such as an assistance ring independent or associated with a microkeratome suction ring. These physical reference assistance devices are also relied upon in the prior art for video referencing when tracking an ablation application sequence. It is preferably, however, from the standpoint of avoiding added patient discomfort, physical obstacles and visual obstacles during an ablation application sequence to be free of such mechanical assistance devices.

The present invention is directed at avoiding the aforementioned drawbacks and features an eyetracking system that advantageously utilizes the natural, inherent characteristics of an eye including the eye's peripheral field vision tendency to pull in images toward the focal point of the eye. The present invention includes a reference marker device that preferably projects its reference marking on the iris at a location external to the pupil to take advantage of the iris' color contrast and to enable the utilization of the pupil for facilitating a visual determination of an eye tilt situation. The present invention provides non-invasive reference marking(s) through application of a reference beam that is reflected in the iris with the reference beam being visible light or some other wavelength (visible or non-visible) such as an HeNe laser beam or an infrared beam. The reference marker(s) or marking means are then compared against an easily determinable reference such as the center of X, Y generated video capture grid and to the center of the pupil which is determined for example by the video frame capture analysis software by determining a major/minor axis intersection on the displayed pupil (the major/minor axis application accommodating for elliptical or other non-circular pupil shapes). This technique allows for ready determination of eye tilt and thus avoids eye tilt induced errors either in the original reference frame capture or in subsequent tracking.

To illustrate the potential error which can be introduced into an eyetracking and ablation application system, reference is made to FIGS. 3 to 6. FIGS. 3A and 3B illustrate an eye that is centered with respect to an X-Y axis plane which can be considered the reference location for purposes of the following discussion, and is also the appearance that would be seen through the ocular lens of the microscope which corresponds with the video frame setting. Hence, FIG. 3A is illustrative of a planar view through a microscope ocular of a patient's eye while FIG. 3B is illustrative of the physical orientation of that eye. The "A" and "B" designations for the additional FIGS. 4, 5 and 6 similarly depict the ocular view and a schematic physical eye orientation as well. FIGS. 4A and 4B illustrate a non-tilt shifting of the eye along an assigned +Y axis direction, while FIGS. 5A and 5B illustrate a non-tilt shifting of the eye along an assigned +X axis. A shifting of the pupil along the X-Y plane is due to head and body movement, while pupil movement with respect to a stationary head is due to the eye tilt. It is this eye tilt which is problematic to surgeons and it is eye tilt that prior art tracking systems are inadequate in handling. Thus, even when the head is held relatively stationary by a cervical pillow or some other head holding means, the prior art problem of inadequate eye tilt tracking still exists. Hence, it is of importance to be able to adjust for eye tilt whether the head is held stationary or not.

Figure 6A:
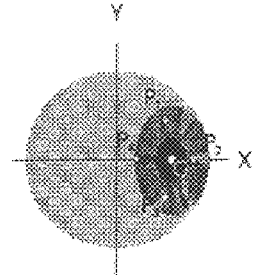
FIG. 6A shows the eye in FIG. 3A following a tilt without any shift along the X-Y plane.
Figure 3B:
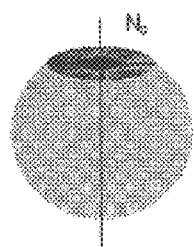
Figure 4B:
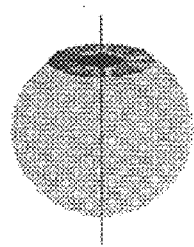
Figure 5B:
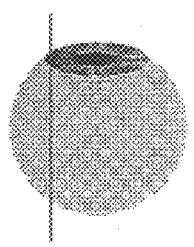
Figure 6B:
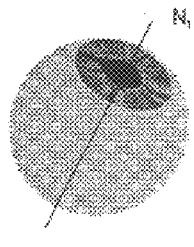
Figure 3C:
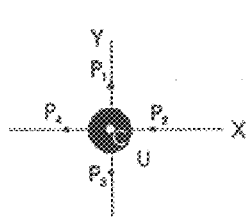
Figure 4C:
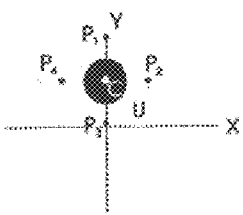

FIGS. 6A and 6B illustrate a centered eye that has tilted along the +X axis, which is just one of many possible tilt orientations of the eye within the 360° range represented by 90° quadrants Q1 to Q4. While not shown, a combination of a shift and tilt is also possible such as when both the head shifts and the eye tilts within its socket. With the present invention, a combination eye tilt and eye shift situation can be analyzed to determine both the eye shift and eye tilt component of that combination.

Reference is now made to FIGS. 7A and 7B with FIG. 7A showing a schematic depiction of a laser beam application to an eye that is in +X the tilt orientation shown in FIGS. 6A and 6B as well as a corresponding tilt along the −X axis. FIG. 7B illustrates a schematic depiction of the resultant error caused by the energy density variation that is induced in the cornea of an eye during a standard astigmatic ablation pattern application. As can be seen from FIGS. 7A and 7B, because of the orientation of the eye there is a higher density applied on the portion of the surface tilted closer to the laser beam than that surface which has shifted away from the laser beam (e.g., the shadow side). In a standard astigmatic treatment process the cylindrical ablation pattern E is applied by the laser and downstream laser components (L). As shown in FIG. 7B, the laser beam application of pattern E to a tilted eye introduces error by varying energy density values across the beam reception area of the eye. In FIG. 7B this is represented by the "hot" and "cold" representations in the tilted eyes wherein the non-tilted eye has received the desired energy level based on an earlier determination as to how the eye is to be ablated.

FIGS. 3C to 6C provide an illustration of one of several possible referencing patterns provided to the eye by the referencing means of the present invention. These figures also help to illustrate the deficiencies in the prior art systems in their inability to differentiate between eye adjustments due to tilting (e.g., see FIG. 6C) and eye adjustments due to shifting (see FIGS. 4C and 5C) or eye adjustments due to a combination of the two. For example, in prior art systems such as described above and represented by FIGS. 1 and 2, and with the central point C the intended target, the eyetracking system would simply determine +X and +Y adjustment requirements for each of the situations illustrated in 4A, 5A, and 6A and then trigger a non-aligned laser beam application such as those depicted in the left and right views in FIG. 7A and by 22' in FIG. 1.

If the FIG. 6A illustration happened to be the position assumed by the eye at the time of reference determination and the operator adjusted the patient bed or headrest on the belief that a shift was required for centering, then the subsequent ablation procedure would be subjected to a significant initial error that would carry over to subsequent ablation applications. This is even possible with some of the more advanced auto initial alignment check systems on prior art laser systems, as the pupil center of the tilted eye, once shifted over by the operator within the cross point for the cross hairs of the video image of the eye would consider the pupil to be sufficiently centered to provide for initiation of laser ablation, when it is actually far from being centered upon assuming a non-tilt orientation. Also, even upon a proper initial referencing of a non-tilted eye a subsequent tilt during laser ablation particularly with large scan beam applications, can lead to the varied density error represented in FIG. 7B.

Figure 5C:
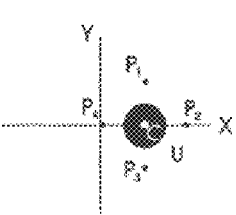
Figure 6C:
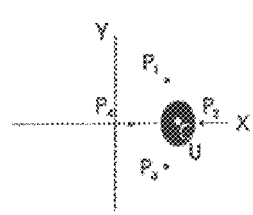

A review of FIG. 6C provides an initial illustration of one feature of the present invention in that it can provide a readily apparent indication to the operator (and the video detection software as described below) of a non-alignment being involved prior to a reference capture command. That is, a comparison of, for example FIGS. 5C and 6C illustrates that when a tilt is involved the center point C becomes non-centered with respect to the four reference points P1, P2, P3 and P4 spaced about the point C while a non-tilted, shifted eye maintains point concentricity. As will be explained in greater detail below, the non-centered relationship amongst the points also provides means for determining the angle of tilt of the normal axis of the eye from a non-tilt reference location and hence information can be passed on to the laser ablation control system to provide for an accommodating normal eye axis tilt in the laser beam delivery system. At the same time an analysis can be made to determine if, in addition to the detected amount of tilt, there exists some non-tilt (shift) movement in the eye which can even take place with a head held in position by a cervical pillow or the like although to a much lesser extent than a non-fixed head.

FIGS. 8–9 illustrate a first embodiment of the present invention. FIG. 8 shows a block diagram of one preferred embodiment of a laser system with a preferred active eyetracker system used in conjunction with a conventional laser delivery system. The block diagram in FIG. 8 illustrates one embodiment of an ophthalmic laser surgery system (108) of the present invention, while FIG. 9 provides a schematic physical presentation of that which is shown in FIG. 8. As shown in FIGS. 8 and 9, laser beam 111 is delivered by laser 110, which is preferably an excimer laser outputting ultraviolet light at a wavelength of 193 nm, although other ultraviolet energy wavelengths suited for ablating corneal tissue can be relied upon in the system shown in FIG. 8.

The laser beam outputted by excimer laser 110 can be a large spot laser beam such as, for example, that provided by a Lambda Compex Model 205 excimer laser manufactured by Lambda Physics GmbH, located in Gottinggen, Germany from which there can be generated a circular beam with a diameter of 6 to 10 mm (which is well suited for accommodating most eye configurations) and outputs a pulse in excess of 400 mj which is sufficient for corneal ablation. An 8 mm diameter large beam with an energy level of 400 mj or higher is particularly well suited for the preferred applications of the present invention. While a large beam application is preferred under the present invention, the eyetracker system can also be utilized with a flying spot laser delivery system.

The laser beam 111 output by the laser is passed through a beam splitter 112 where a small quantity of the UV light is reflected by the beam splitter to be input and measured by the energy monitor 130. The energy monitor 130 then inputs the monitored energy information to main computer or main processor 132 where a comparison is made between the actual energy being output by the laser and the desired energy level, and the processor directs an adjustment signal to the laser's voltage source to effect any adjustments needed to maintain a constant energy level.

The UV light passing through the beam splitter is directed to safety shutter 114 preferably in the form of a mechanical, physical light beam blocking device. The safety shutter is placed "on" when the system is in surgical mode and is placed "off" in a blocking position whenever the processor receives an input from one of the laser system's components suggesting a device is not working within established parameters or upon an operator's activation of an emergency shut off.

During a non-shut off state of operation, the UV light beam 111 is directed to turning mirror 121, which can be either a fixed or a scan mirror (e.g., a single or dual scan mirror) so as to travel in a straight line to eye 128 (e.g., the exposed corneal surface being ablated). For initial focusing purposes, there is utilized non-ablating beams such as the red HeNe laser 139 with a wavelength of about 632.8 nm and Green HeNe laser 140 with a wavelength of about 543.5 nm. A third HeNe laser 120 of about 632.8 nm is typically further relied upon for patient fixation. As the third HeNe laser is used for patient fixation, it is aligned with the patient's eye and the alignment lasers.

FIGS. 8 and 9 further illustrate the use of a video camera system (137) provided to show to the surgeon the patient's eye in a color monitor (138). This video camera can be one in the same with the eyetracker camera described below, although two separate camera's or similar functioning visualization/image capturing equipment is preferably utilized due to the different intended functions of each. Initial positioning of patient is realized by a micro-processor controlled bed (146) that responds to commands generated by a joystick (144) which moves the patient bed on the axes X, Y and Z and interlocks the patient bed when the surgery is in progress. The patient bed is also interfaced with the main computer via computer interface (142). Prior to surgery, the patient (148) is accurately examined by a topographer (150) and/or an aberrometer (152) or any other type of medical device for analyzing the optical structure of the eye, and the information generated by the analyzer is then transferred to the main computer (132) which executes a software program and generates the customized cornea ablation pattern deemed best suited by the surgeon for achieving the desired correction. In this regard, a customized volumetric ablation pattern based on, for example, a stored, ophthamological patient data set (e.g., a volumetric ablation data set as described in U.S. Pat. No. 6,129,722 which issued on Oct. 10, 2000 to Dr. Luis Ruiz which patent is incorporated herein by reference) which data set is developed by a measuring instrument such as a topographer and/or aberrometer. Under the present invention, the volumetric ablation data set is provided to a processor for input to, for example, a pixel based mask system via a digital interface, or some other ablation volume formation means. The analyzer of the eye characteristics information can be a component of the overall system or can be a remote sub-system with the volumetric ablation pattern data set deemed best suited for that patient being stored by the main computer either by way of a direct feed to the main computer from the analyzer or stored on an appropriate storage medium for transfer to an input of the main computer, or transferred remotely from one location to another through any suitable information transmission means such as a telephone line.

As shown in FIGS. 8 and 9, eyetracker system 136 includes marker system 117 which is preferably a satellite light marker system that takes advantage of the natural design of the human eye by utilizing the cornea's natural ability to converge objects to the eye's focal point and in utilizing the color contrasts between the iris, sclera and pupil of the eye. Utilization of the color contrast is useful both with respect to the visual image presentation through the microscope and in the video analysis process wherein the natural contrast between the sclera, iris and pupil of the eye (such as the pigment contrast in the visible light spectrum) facilitates the image to image comparison process by the video analysis software. Satellite marker system 117 is also designed to be a non-invasive referencing means (e.g., avoids reference ablation formation in the eye and/or applied dyes to the eye and/or placement or reliance on a physical assistance device such as a physical assistance ring structure either by itself or as a component of another device such as a microkeratome). The above reference to "satellite" is intended in the sense of having the marker generating means free from contact with the eye and the structural components supported by the patient's head and external to the ablating laser beam path. In a preferred embodiment, the marker generating means is also positioned so as not to interfere with the microscope view relied upon by the surgeon to view the surgery.

Satellite marker system 117 of eyetracker system 136 is shown in FIGS. 8 and 9 to comprise a plurality of satellite reference markers 118 which each direct a reference beam of light to the eye. As explained below, to provide a dual function illumination and marker device, the markers preferably operate in the visual light spectrum. However, alternate wavelengths (visible and invisible) can be utilized such as, for example, non-ablating, visible HeNe lasers and similarly non-invasive infra-red lasers. The eyetracker camera relied upon is designed to operate in conformance with the type of reference marker means utilized, including the possibility of two reference marker applicators of different wavelengths and a switchable eyetracker camera or two corresponding cameras.

In a preferred embodiment of the invention there are at least three and more preferably four or more individual satellite point reference markers such that concentric variations can be determined to differentiate eye tilt from eye shift. The satellite point markers are positioned to direct their respective beams so that there are projected onto and reflected from the iris region of the patients eye. The angle of incidence of the reference marker beams is also preferably made so as to reflect up into the visualization field of surgical microscope 125 and is also directed into the pick up field of the eyetracker camera 141 through use, for example, of a beam splitter (not shown). The reference points generated by the light point markers 118 are applied so as to fall within the iris region of the eye to take advantage of the contrast enhancement provided by the iris as well as the good visual range characteristics in the iris region (e.g., easily visible in the microscope and having an X-Y plane ring area able to fully accommodate a full range of pupil movement due to eye tilt). This means, that the preferred positioning of the light point markers is outside the potential dilation range of the pupil and internal to the outer periphery of the iris.

This strategic positioning of the satellite marker system 117 is unlike the conventional illumination systems (such as a general use microscope illumination ring or left and right fiber optic illumination lights) in that the present light markers are strategically positioned for the eyetracking functioning described in greater detail below. These markers, however, when using visible light, also provide the additional function of illuminating the operating area. Accordingly, the present invention is highly advantageous in providing components with dual functioning capability. Moreover, the preferred visible light markers of the present invention do not have the prior art limitations as to the range of visible illumination to be used in conjunction with the infrared or UV light beam sources relied upon in the prior art eyetracking systems (with such error being induced by the natural presence of some UV and infrared wavelengths within the visible wavelength range of illuminating light(s) and the potential for confusion due thereto in the eyetracking process). In fact, with the dual functions of illumination and eyetracker referencing provided by the present invention's marker means, the greater the intensity of applied visible light, the better the illumination and marking reference contrast.

Light point markers 118 can be relied upon as the sole marker referencing means of satellite marker system 117 for use by the eyetracker system in following movement of the eye. Alternatively, or as a supplement thereto, the marker system 117 comprises ring light marker device 127. In this regard, reference is made to marker system 117 in FIGS. 8 and 9 which is shown to comprise both satellite marker system 117 and ring marker device 127. Ring marker device includes a light projection device that preferably also works in the visible light range, although other light wavelengths (visible and nonvisible) such that those noted above as workable for the point markers, are also workable with the ring light marker. Alternatively, a combination of two different wavelength marker devices can be utilized. For example, the reference point marker device can operate with an infrared wavelength while the ring marker device operates in the visible range (or vice versa) with the eyetracker camera being switchable for comparison purposes. Ring marker device 127 generates one or more marker rings, again preferably within the iris and, as above, preferably between the outer periphery of the iris and an internal boundary defined by the maximum pupil dilation diameter as determined by typical eye measurements for adult maximum pupil dilation diameters and maximum iris diameters. An inner diameter of 6 to 6.5 and an outer diameter of 8 to 8.5 mm would be well suited for positioning the reference marker points and/or ring(s) within the always visible iris portion of the eye.

Suitable point reference markers include fibre-light illuminators which are available on the market (e.g. from Edmund Industrial Optics in Barrington, N.J. U.S.) as well as suitable focusing and fixation supports which provide the appropriate focused spot size and orientation with respect to the eye (e.g. 45 to 90 degree angle of incidence with four lights at 90 degree equal spacing with the main beam axis of the lights' output lying at equally spaced points along a circumference) so as to have the points project on and reflect off the iris at locations that are also preferably coinciding with the video and microscope cross-hairs.

A suitable ring illuminator can include a fiber optic ring light guide together with a suitable co-axial fixation support to achieve the desired projection diameter on the iris of the eye being simultaneously illuminated with that light. Fiber optic ring guides are available from Edmund Industrial Optics. Preferably, the ring guide is positioned coaxial with respect to the reference beam axis so as to function both as a reference marker and as a source of illumination for the surgical area and also for the surgical microscope 125.

Reference is made to FIG. 10 showing an iris and some preferred locations for the reference points and/or ring(s). As shown in FIG. 10, reference point C is preferably utilized and typically is taken at the geometric center of the eye pupil or at the visual axis intersection in the pupil of the eye (and is preferably determined through use of, for example, the aforementioned major/minor axis application technique during captured video frame analysis). In FIG. 10, reference points P1, P2, P3 and P4, naturally assume a concentric orientation with respect to center point C due to the natural ability of the eye to focus the reference marker image toward the focal point. The reference marker device(s) are also preferably set up such that the points fall on the respective +/−X and Y reference axis extensions (points shown positioned at the 0°, 90°, 180° and 270° marker locations for one particular chosen degree set which can vary depending on the chosen orientation and which eye is involved). The same X, Y axis extensions would also be viewable in the microscope image of that eye as well as in the video image of that eye (i.e., the cross-hairs) with all parameters being related to center point C which is representative of the base target point of the laser system.

As further shown in FIG. 10, pupil U has a radius defined by its periphery R1 (at a current dilation level). The points P1–P4 are shown arranged along the circumference ring R3 which has a radius well within the range of visible iris despite varying dilation levels of the pupil (e.g., a radius that fall ½ of the way between full iris radius represented by ring R5 and the maximum pupil dilation radius having circumference $R_1$). If a single marker ring is relied upon that ring could also be set so as to have the radius of ring R3. In a preferred embodiment however the reference points are used either alone or in conjunction with one or more marker rings. Having one or more ring markers in addition to point markers provides a back up means for eyetracker positioning purposes in that the active eyetracker can switch from, for example, the reference marker points in the eyetracker position analysis to a ring reference mode for comparison purposes. This back up can either be in the context of always running both modes (point reference mode and ring reference mode) or initiating the former or latter whenever a system problem is detected such as, for example, a burnt out reference light. This type of backup can be based, for example, on a self diagnostic check system which monitors the direct status of the environment for any significant change in photo array sensor 135 or monitors the general environment for any significant deviation at a location not subject to operator or equipment shadow problems.

FIG. 10 further illustrates some preferred locations for ring marker locations when used in conjunction with the reference point markers or when free of the latter. These locations are referenced by rings R2 and R4 with R2 being internal to the reference point circumference R3, and R4 being external to R3. In addition, to providing a back up source to supplement the reference point markers, one or more added rings also facilitate rapid visual appreciation for shifts and tilts in the patient's eye as well as some general information as to the range of movement or tilt degree. Again, however, reference can also be placed on one or more reference rings free of the point markers.

Thus, for a typical iris diameter R5 of 10–12 mm and a representative pupil size of 2 mm to a maximum 6 mm (depending on the pupil dilation state—although in the present invention, unlike some prior art techniques which require the extra step of induced pupil dilation, the pupil is at a natural, minimal state with the preferred level of illumination) the reference markers are advantageously positioned within a range of 6 mm to 10 mm. That is, the eye's natural characteristics provide an adequate range of iris area for forming the point markers such as in a circumference diameter range of 7 to 9 (more preferably 8 mm±2 mm). This range would also be the preferred range for a marker ring. If a ring marker and a point marking technique are used together, than an outer circle and/or inner marker ring circle arrangement is preferable with the diameter of the inner and outer rings being within a +1 mm to +3 mm range of the point reference circumference (e.g. R2 with a 6.5 mm, R3 with an 8 mm, and R4 with a 9.5). The typical video view reference frame typically is large enough to encompass the sclera represented in FIG. 10 by R6 which typically has a diameter of 25 mm.

FIGS. 10A and 10B illustrates a geometric circular zone configuration and an ablation volume pattern designed for presbyopia corrective laser surgery as described in PCT Application No. PCT/US99/26242 filed Nov. 8, 1999 to Dr. Luis Ruiz and which designates the U.S. This PCT application published as WO/27324 and is incorporated herein by reference in its entirety.

FIG. 10A illustrates geometric circular zones representing ablation volume to be provided with predetermined specific characteristics. FIG. 10A illustrates four distinct zones with circular zone A being centered on the desired central point for the unablated area and having diameter I (mm). Inner annular zone B has outer diameter H (mm) and shares a common boundary with zone A and thus has an internal diameter I (mm). Intermediate annular zone C has an outer diameter of G (mm) and an internal boundary in common with the exterior boundary of B which is of length H (mm). Outer annular zone D has an internal diameter in common with the outer boundary of zone C of diameter G (mm) and an outer periphery having the illustrated diameter F (mm). The outer diameter is preferably taken from limbus to limbus which is typically about 10.5 mm.

Internal circular zone A, which is centered about a desired central point of the patient, as described below, and has diameter I (mm), represents the zone which is to be kept free of any laser activity by, for example, mask positioning or controlled avoidance of ablating laser contact within that zone. Zone B, with outer diameter (mm), represents the maximum ablation (or removal) depth zone. Maximum ablation depth represents the corresponding correlation between diopters (i.e., 1/focal length, m) and the maximum depth of ablation of tissue in microns. Zone C represents the ablation perimeter limit that covers all of the ablation treatment zone. The outermost periphery of zone D of diameter F is represented by the limbus to limbus diameter.

The profile shown in FIG. 10B illustrates an ablation pattern for the laser system that is highly effective in removing the presbyopic effect. As shown in FIG. 10B, zone A is shown as a flat, horizontal line due to a zero ablation effect on that region. FIG. 10B shows at the peripheral edge of zone A having a radiused (convex) edge which leads into a relatively steep, slightly concave, drop off profile section which extends to the maximum ablation point MD of the profile. Out from the maximum ablation point, there extends a smoothly curving ablation profile portion that is less steep than the drop off profile section (i.e., an aspherical relationship wherein the inner MD and outer MD slopes do not correspond) and extends from the maximum ablation depth out to the outer perimeter of zone C. As shown by FIG. 10B, a straight line approximation of the slope differential between the profile section extending out from point MD and in toward point MD is represented by $RP_1/r_1$ and $RP_2/r_2$. Since depths $RP_1=RP_2$, the ratio of slope difference can generally be said to be represented by $r_1/r_2$ or (G-I)/(H-I). Also, the profile section that is defined by the lower quarter depth sections of the inner curvature portion leading to the maximum ablation point and the outer curvature portion extending off from the maximum ablation point represent a concave, cup-shaped section within the lower quarter of depth region, with about ⅓ of the area of that cup-shaped section being inward of a vertical line extending through the maximum ablation point and the remaining ⅔ of that area outward thereof. The remainder of the less steep curvature extending over the remaining ¾ of depth has a smooth convex configuration which blends into the unablated area extending outward from zone C.

In general association with the illustrated profile in FIG. 10B, the following shows the preferred values and ranges for the diameters F, G, H and L.

F=limbus to limbus determination (approximate 10.5 mm)

G=7.4 mm (preferred range of about 7.0 to 7.8 mm)

H=2.8 mm (preferred range of about 2.4–3.2 mm)

I=1.6 mm (preferred range of about 1.4–1.8 mm)

The maximum ablation depth for the preferred profile contour is about 38 microns and a preferred range of depth is about 34 to 42 microns.

FIG. 10C provides a schematic illustration for determining a desired nasal-superior center NS point for the circular non-ablation zone A shown in FIG. 10A. In FIG. 10C the left eye pupil P is shown schematically together with nose N of the patient. The up and down arrows illustrate the superior and inferior half sections with horizontal line $L_1'$ and vertical line $L_2'$ passing through center point CP of pupil P. Lines $L_1'$ and $L_2'$ break up the pupil into four quadrants with quadrant Q representing the nasal-superior quadrant of the pupil. The radial lines R1' and R2' defining quadrant Q are divided into thirds by points $P_1'P_2'$ and PA, PB. Nasal-superior point NS, which represents the center point for zone A, is defined by the intersection point for the lines extending from the points $P_1'$ and PA and into quadrant Q. Thus, for a typical undilated pupil diameter D1 of about 2 mm, the unit length out to each of $P_1'$ and $P_2'$ is 0.33 mm. It has been found that this center point NS for the non-ablated zone is preferred in the presbyopia correction process. Thus, following establishment with the reference marking means of the initial reference parameters, a supplemental reference cross hair set CH is positioned (e.g., click and mouse adjustment of a supplemental, different colored cross-hair depiction) to presbyopia center point NS. Similar shifts might also be deemed clinically necessary as determined by the surgeon, and typically require a laser delivery system override command from the surgeon. The laser beam delivery system thus places the applied laser beam pattern based on the supplemental reference set centered on points NS while the eye-tracking system can still refer to the base or original reference values for monitoring eye shift and tilt. In this way the ablation pattern is applied concentric about this presbyopia based ablation center point NS and also maintains tracking conformance with a moving eye.

In a preferred embodiment of the invention the laser system provides automatic adjustment means which provide an automated setting of this presbyopic correction center point by way of a software based option presented on a monitor or the like wherein the surgeon can simply choose this presbyopia based centerpoint. The eyetracker system (e.g., the video analysis means) can be used to implement this shift following an initial analysis of the pupil during the stage of initial reference parameters determination.

Figures 11A, 11B, 11C, 11D:
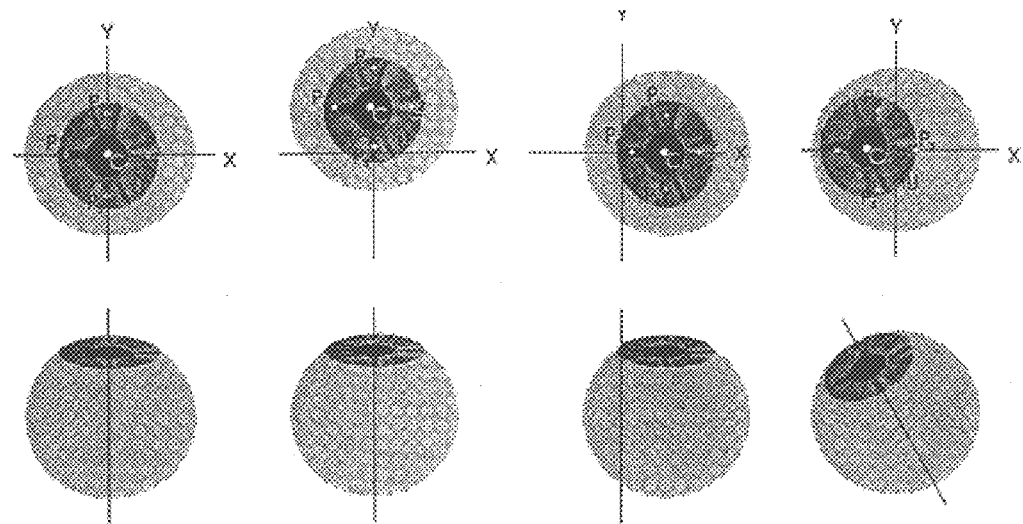

Reference is made to FIGS. 11 to 13 for a more detailed explanation as to the function of the reference point markers and/or ring markers in use to determine eye tilt and which are readily useable together with, for example, an eyetracker camera system (e.g., X-Y axis based camera with cross hairs provided in the picture frame) for more complete eyetracking capabilities. The upper half of FIGS. 11A, 11B, 11C and 11D show how the eye appears through an ocular of a microscope having applied cross hairs with the point referencing means of the present invention in use, while the bottom half provides a side elevational view of the eye. With the use of a beam splitter or the like the view of the eye through the ocular of the microscope corresponds with the video reference frame such that the cross hairs in the ocular of the microscope coincide with that used in the video reference frame as discussed below. In FIG. 11A the eye is in a non-tilt orientation and has its center coincident with the cross hairs' intersection at point C. FIG. 11A is illustrative of a typically preferred reference start location for the first video capture reference frame as well as a designation of the laser system that it is ready for an ablation process start (e.g. the system beeps to indicate that the parameters are acceptable for laser ablation). With the aforementioned off center presbyopia ablation center NS, the surgeon would then shift a supplemental cross-hair set inked by software to the ablation delivery means for application by the ablation delivery means with reference to the non-central axis starting point NS.

FIG. 11B shows an example where the eye is positioned along the +Y axis to the upper edge of the visual field of the microscope ocular, which might be a situation where the patient is initially being moved into the desired reference point prior to the start of a surgical procedure or a situation subsequent to that wherein the patient's head or whole body has shifted from an initial reference location which could be in the midst of a laser ablation procedure. In this latter situation, the active eyetracker system would take this +Y shift into consideration in first determining whether or not to fire (i.e., whether a permissible range of movement is involved) and, if so, shifts the beam application to coincide with the +Y shift. As described below, this shift can alone entail movement of a scan mirror or adjustment of a pixel set.

FIG. 11B also shows a non-tilt orientation. Because of the non-tilt orientation the reference markers are equal distance from the reference center point of the eye (e.g., the center point of the pupil), despite being off the video/microscope cross hair intersection center M (FIG. 11D). This is based on a human eye's natural ability to direct images (light beams in this case) that are within the 180° semi-spherical field of vision to a centered, concentric location with respect to the pupil whether the light source is already centered or off center. This concept is discussed in greater detail below with reference to FIGS. 12 and 13.

FIG. 11C provides a view similar to FIG. 11B except the non-tilted eye is in a +X axis shift relationship with respect to the set video/microscope reference frame. Also, as with FIG. 11B, the point reference markers in FIG. 11C are equally spaced along the corresponding X and Y axis extensions to show a non-tilt relationship despite the fact that the eye is offset from the video/microscope frame center M. The reference point markers are preferably set along the X and Y axis to allow for a reference view along the measurement line designations along the cross hairs of the video and microscope ocular. This adds a ready visual guide to the surgeon as to the degree of tilt involved based on the degree of off centering of one or more reference markers. As explained below, the eyetracking system is able to also analyze the amount of off centering with respect to the tilt reference point markers (e.g., a software program carrying out an analysis of the captured video image and the relative positioning of the markers with respect to a reference point such as the center C). This includes, for example, a sequence where in a first step the video frame analysis program determines whether the center of the pupil has deviated from a concentric relationship (or beyond a preset range of acceptable nonconcentric deviations). If so, the video frame analysis program then proceeds with a calculation of the tilt angle associated with that deviation. FIG. 11D illustrates an example of an eye that has tilted only (i.e., there has only been a tilting of the eye and no head or body shift producing an X-Y axis plane shift). As can be seen from FIG. 11D, despite the non-movement of the head, the tilt of the eye causes a shift of the central point C in a –X axis direction, which is also the direction of tilt rotation. Due to the natural optical effect of the generally semispherical cornea, the reference markers appear within the iris in an offset fashion. As the tilt is along the –X axis (amongst the 360 degrees of radial tilt possibilities) in this example, the reference marker point $P_4$ along the –X axis appears in the video/microscope image as being closer to the pupil center point C than in the non-tilt/non X-Y axis orientation in FIG. 11A, while the opposing point reference marker $P_2$ appear farther removed from center point C.

A marker system involving a ring marker would also both provide a visual depiction of whether a tilt or non-tilt situation exists due to a change in concentricity and a means for determining by way of the eyetracker system whether the eye has tilted and, if so, to what angle and in what new orientation. That is, the change in concentricity of the marker ring and the pupil center, for instance, can be analyzed by analyzing various shifted points amongst points on the ring pattern and the reference center C. The present invention thus features marking means for presenting tilt information based on the interaction of reference markers with respect to each other and a common reference (preferably center) point, with a change in the relative relationship between the common reference point and point markers occurring only during eye tilt and not (at least to an appreciable extent) in non-tilt X-Y plane shifts of the eye.

FIG. 13 illustrates the above described ability of the eye to always place (at least within the general range of potential X-Y shifting of an eye during laser surgery) the reference marker points (shown landing in the preferred iris location) in a concentric relationship with respect to the pupil and the center thereof which is an arrangement which makes for efficient eye tilt calculation. In FIG. 13 there is shown +X and –Y shifting of the eye in the X-Y horizontal plane without tilt. FIG. 13 also shows point marker reference lights L1 to L4 and a schematic depiction of light rays originating from the respective sources of L1 to L4. As shown in FIG. 13 despite the different locations of the eye in the X-Y plane the light rays coming from the light sources L1 to L4 land within a concentric ring with each of corresponding reference marker points P1 to P4 being of equal distance to the pupil and equally circumferentially spaced in each instance. This means that the light bank of pointers represented by reference lights L1 to L4 could be located in a variety of locations and the eye would still pull in the rays into a concentric ring. However, to provide the sharpest (non-elliptical/precisely circular) reference point depiction in the captured video image, the main axis of the reference lights structure (and the exiting light beam) are preferably placed at about a 60 degree angle of inclination (as compared to other angles of outlet that are still capturable by the eye and thus functional, but tend to provide a slight elliptical configuration in the reference mark or point in the eye image). In addition, it is preferable to position the lights (e.g., the height from the eye and the diameter of the circumference for the equally circumferentially spaced exit points of lights L1 to L4) so the light beams of the respective markers are pulled in and appear on the iris as background as discussed above for FIG. 10. As also explained above, the reference pointers can be replaced by a light ring (although the reference marker point embodiment is preferable from the standpoint of sufficiently determining tilt with a minimized number of points about a circumference). Three points might also be used, but this is less preferable in that the four points allows for reference locations on the cross hairs of a video frame or microscope and more readily conveys the nature of the tilt.

FIGS. 10 and 13 show an applied light ring marker on the iris extending at a common circumference with the reference points (see FIG. 8 for an illustration of a light ring marker device). In addition, one or more ring markers of a different diameter can be used together with the point reference markers for purposes, of simultaneously running backup checks (e.g. analysis of ring concentricity variations within a certain range) or as a fail safe mode in the event of a point marker light going out between ablation pulses.

FIG. 13A provides an additional illustration as to how the reference point marks deviate in accordance with the tilt of the eye's normal axis. As can be seen in FIG. 13A the greater the degree of tilt, the closer the center of the pupil moves toward one reference point and the farther it moves from the opposite point mark. Also, the same closer/farther relationship between the two opposing points is maintained for an eye that has shifted, but retained the same tilt orientation from one shift location to the next. It is also preferable to have the point markers positioned such that at the maximum angle of tilt the farthest out point marker still projects on the iris, although at a point preferably just inward (<0.3 mm) from the iris periphery, while the closest point marker also stays on the iris, although at a point just outward (<0.3 m) from the maximum dilation state of the pupil (e.g., a 6.0 mm to 6.3 mm range).

FIGS. 12A, 12B and 12C show schematically the variation in viewed reference marker location due to a tilt in the eye. FIG. 12 A shows a "normal" eye position that has a normal axis No in a non-tilt orientation and coincident with respect to the line of the incoming reference position laser beam and hence also the video frame/ocular cross hairs. FIG. 12A also shows a tilted eye having its normal axis shifted from the No to N1 position. FIGS. 12B and 12C show, respectively, the corresponding reference marker locations for the normal and tilted eye depictions in FIG. 12A. As can be seen when the eye tilts in the manner shown in FIG. 12A the resultant optical changes result in the planar image of the eye showing the pupil having moved closer to one (or two if the tilt is not along only one reference axis) of the reference markers and farther away from the opposite reference marker on the same axis.

FIGS. 12B and 12C also show the relative measurable shifts in the distance between the preferred center reference point C and the points P1, P2, P3 and P4 which shifts are detectable in the video image frame and thus can be monitored by the eyetracker system. Through measurements and analysis of the deviation of the distances amongst the noted distances D1, D2, D3 and D4, the degree of tilt can thus be determined by microprocessor 132 through any one of a variety of ways through use, for example, of standard geometrical mathematical formulas. In other words, once a determination has been made that the eye has tilted by way of a review of the relative positioning of the pupil center and the reference means of the present invention, a determination can be made as to the associated tilt angle. There exists a variety of different ways of determining the tilt angle following a determination in accordance with the present invention that a tilt is indeed involved and not solely an X-Y axis plane shift (which shift can even occur to some extent with head fixation devices such as a cervical pillow).

One preferred technique is shown in FIG. 12D and involves utilizing the relatively universal value for an adult focal radius (see focal point Fc) of a cornea Rc (11.25 mm) in conjunction with the also relatively standard length between the eye's center apex Ca point and the iris plane IP (3.5 mm) otherwise known as the anterior chamber depth Ac. With Rc−Ac=7.75 mm and the video analysis determination of the pupil center's shift ΔU (shown along only the X axis in this instance, but could also have a Y axis component or could be only a Y axis shift) the tilt angle Θ can readily be determined based on tan Θ of ΔU/7.75 mm. Alternatively, the eyetracker system can refer to a stored memory bank for various angle interrelationships between various differentials between the pupil center (or whatever reference point is being used) and the values of D1,D2, D3 and D4. It is noted that with respect to an X-Y-Z reference frame that is held at the "No position, there is a slight Z-axis shift in the pupil made possible by the reference marker means of the present invention. This is a neglible amount for the typical range of eye tilt involved and thus can be ignored during angle determination. Alternatively, sophisticated conventional geometrical analysis techniques can also be relied upon in determining the angle Θ, including those sufficient to take into consideration this minor Z axis shift in calculating Θ.

FIG. 12E provides a flowchart for an eyetracker system based on the reference marker means for determining whether tilt exists and, if so, the tilt location and angle. As shown in FIG. 12E the eyetracker system conducts a self diagnostic test determination whether the reference marker means are properly operating (on and at the proper illumination level). If not, the operator is alerted that a reference marker problem exists and the laser system prevented from operating.

If the reference mark pointers are operating properly, the eyetracker system can carry out a captured frame tilt analysis. In so doing, a check is made as to whether the pupil center has tilted or not. For example, check as to whether a D1≅D2≅D3≅D4 (the≅designation being indicated in the event some minor tilt tolerance is deemed acceptable before a tilt mode is considered to exist). If no tilt is determined to have occurred, a laser pulse can be fired following any required aiming step.

If a tilt is deemed to have taken place based on, for example, $D_1$ not being equal to $D_3$, then the eyetracker system proceeds with an analysis of Δµ and Θ relative to the X-Y axis plane and generates and forwards an appropriate signal to the laser delivery system. If D2 D4, then a determinant of Δµ and the intersection of $N_1$ relative to the X-Y plane is determined together with Θ. The appropriate signal is then delivered to the laser delivery system. If D1=D3 and D2=D4 then a no tilt signal is generated. If D1=D3 but D2=D4 then Δµ along the Y-axis and the corresponding Θ tilt in the eye axis movement from No to $N_1$ is determined.

FIG. 14 illustrates a series of operator induced head repositioning steps involved in bringing a patient's head and eye to be ablated into focus during the initial positioning and reference frame capture. The view illustrated is that through the microscope ocular, but would correspond in a preferred embodiment with the focusing of the eyetracker camera's video and surgeon's monitor image. As shown by the time sequenced steps 14A,B,C and D, the bed or patient support is typically far removed from focus at the time of starting the process. The surgeon, through use of joysticks 144 or the like, then moves the patient closer into focus until the eye is generally centered within the view. At step C, the eye comes sufficiently into view as to have the reference markers clearly appear on the iris. The surgeon, as well as the eyetracking system, can then monitor/analyze the interrelationship between the reference points and the cross hairs with respect to the pupil, and when the fixation cross point coincides with the center of the pupil a check is made to see if the reference markers are each at a equal distance from the center (or any offset within an acceptable deviation range). If the pupil is sufficiently aligned with the cross hairs, but there is too much off-concentric deviation with respect to the reference markers, the surgeon would know that there is an unacceptable tilt level involved and would ask the patient to fixate on the fixation light (120 FIG. 8) aligned with the laser beam axis until the patient sufficiently removes the tilt in the eye to allow for origin reference capture for use by the eyetracker during the subsequent eyetracking process. Through use of the below described improved ablation delivery system designed to correspond the laser pulse delivery angle with a tilt angle assumed by a patient's eye without the drawbacks associated with moving many large components of the delivery system for large distances, improved ablation results can be achieved. With the below described tilt accommodation laser delivery system there is made possible coverage of all or a substantial portion of the range of possible eye tilt positions (e.g., within an acceptable parameter range preset in the laser system before automatic shut down). In other words, with the below described laser delivery systems designed to accommodate for eye tilt, the tilt detecting eyetracking and laser beam application delivery system can function together so as to compensate for tilting either at the time of initial reference taking and/or at later stages during the laser treatment process.

Also, the initial patient positioning sequence can be partially automated by saving a pre-utilized or factory set bed movement sequence up to for example steps B or C to help speed the process up. The sequence can be made more fully automated through use of an eyetracker video or viewing video focusing adjustment sequence to determine range and offset (which camera can be one in the same in some embodiments) coupled together with automated bed manipulation based on the signal generated during the focusing adjustment sequence. Thus, the video or eyetracker camera or both goes through a series of focusing checks spaced in time between a series of bed movement commands until the bed is adjusted to a location wherein the focusing sequence establishes that the focused eye is positioned within acceptable parameters. In the case of a tilted eye, however, and a laser delivery system not having a level of tilt tolerance at the time of initial reference setting (which tolerance is made possible by the below described eye tilt accommodating laser delivery system), there would still be required an adjustment on the part of the patient to remove the tilt. This tilt removal adjustment can be facilitated at the time of initial patient alignment and first video capture, by a command being sent from a processor receiving eye reference location input, to pulse the eye fixation beam to capture the patient's attention so that the patient focuses on the fixation beam to a sufficient degree to remove the tilt. This would avoid having to have the surgeon remind the patient to look at the fixation light.

Figure 15A:
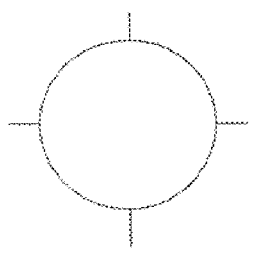
Figure 15B:
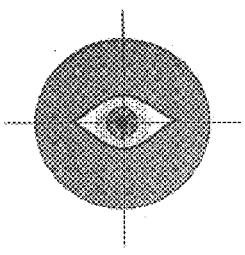
Figure 15C:
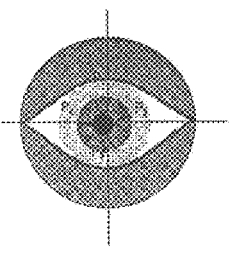
Figure 15D:
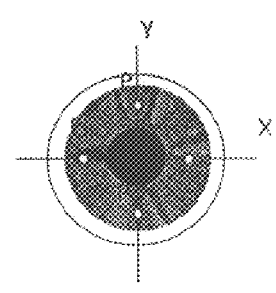

FIGS. 15A to 15D show a series of camera focus level sequences for use in the bed positioning process that would be representative of a series of focus/position checks between patient bed movements implemented through use of the same positioning mechanisms (not shown) triggered by joysticks 144. As shown in these figures, the camera is initially off and then a first image appears in FIG. 15B which as shown is preferably one in which at least part of the eye appears (which can be easily managed through a preprogrammed movement of the bed as discussed above for FIG. 14). The eyetracker camera and associated software then first conducts a focus based analysis of the present image with respect to, for example, the cross hair intersection of the camera or image receiver together with a check against a preestablished parameter reference bank which preferably includes the circumferential ring size of the above noted reference ring and/or point markers (or some other eye feature such as the concentricity and size of the iris). For example, for a normal axis check, a calculation as to the diameter of a ring marker can be made while a check is made in the same step period for deviations of the distance of the point markers from the cross hair intersection. Adjustment signals are then implemented if the present image is outside those parameters to adjust the bed in the appropriate corrective direction followed by another analysis of the location of the eye and the noted reference points with respect to the cross hair reference point and current focus level. This series is repeated until a determination is made that the eye is at an appropriate focus level and in a desired position as represented by FIG. 15D. The focus based positioning process and/or the eyetracking process can also be facilitated by using a view screen point and click (or similar surgeon implemented command) based on a pointer lying within the video image to direct the positioning with respect to an X and Y axis plane. At least during the initial focusing stage, the Z axis positioning of the table can be facilitated with a pop up screen with a range of height adjustment possibilities to start the focus check sequence off at a closer level than might be the situation.

FIGS. 16A to 16D illustrate various eye tilt images presented in different software filter choices available by way of detection software in the computer processor and/or camera. As can be seen from a review of these figures the reference pointer technique which uses the iris background allows for high diversity of settings while still providing clear and readily determinable reference parameters for use in the software analysis of a captured view against an earlier captured reference view. In addition, FIGS. 16A to F also show clearly a situation wherein the eye is tilted (toward the top of the page as presented in FIGS. 16A to F) as can be seen by the relative relationship between the pupil and the four reference pointers. FIG. 16A also illustrates the cross hairs provided in a typical camera and ocular view. The remainder of FIGS. 16B to F have the cross hairs typically present in such views removed for added clarity as to the eye and reference markers.

The above noted information as to the relative position of marker means reference points (or marker reference ring(s)) on the X-Y plane with respect to a chosen video reference point (e.g., the cross hairs intersection in the camera image) and the degree of tilt representation by way of the shift in the relative differences of the reference marker applied by the marking means with respect to the reference center or some other suitable reference, allows for rapid and efficient eyetracking through a picture frame capture and comparison process.

FIGS. 17–19B show a laser system similar to that shown in FIGS. 8 and 9 except for an enhanced laser beam delivery system which is well suited for use with the tilt information obtained by the above described eyetracking system so as to allow for ablations that are more true to the intended results through avoidance of unanticipated tilt based energy density variations as described above for FIGS. 7A and 7B and nonalignment in general. FIG. 17 illustrates mask system 200 placed in the optical path of the laser beam which in this embodiment is a large beam capable of covering the entire ablation area of the eye. An example of such a mask system 200 is found in the liquid crystal mask system set forth in U.S. patent application Ser. No. 09/598,226 filed on Jun. 21, 2000 to inventors Dr. Luis Ruiz and Eduardo Matallana, which application is incorporated by reference in its entirety herein. Another example of such a mask system 200 is found in the various electro-optical masks (e.g. electrochromic and polymer dispersed liquid crystal masks) described in U.S. patent application Ser. No. 09/598,227 filed on Jun. 21, 2000 to inventors Dr. Luis Ruiz and Eduardo Matallana, which application is incorporated herein in its entirety. As explained in greater detail below, these mask systems include optical components in line with active masks that can be used to set desired ablation patterns and vary the overall resultant density level in certain areas of the cornea so as to offset for tilt determinations by way of communication between the active eyetracker system and the mask parameters.

For example, the energy density level for one or more large beam pulses can be altered by way of either turning on or off certain pixels within the mask (so as to achieve a resultant ablation volume closer to the intended tilt results). Transmission densities of certain pixels can also be altered through use of mask system 200 by, for example, a duty cycle variation (variations in on-off states during a laser pulse period) or by changing the level of transmissiveness amongst pixels being subjected to a laser pulse by a change in the blockage/transmission characteristics of certain pixels to compensate for the tilt (e.g., voltage application differentials on a pixel or pixel sub-group basis to achieve various partial transmission blockage levels falling between full block and no block states).

With reference to FIGS. 18, 19A and 19B, 19C, 19D and 19E, a description of the above noted liquid crystal mask system is provided. As shown, active mask 202 comprises a multi-layer assembly 204 which includes first substrate plate 206 of, for example, UV grade synthetic fused silica (i.e., UVGSFS ($SiO_2$)) or sapphire. This transparent substrate plate is followed by a first, transparent electrode layer 208 (FIG. 19B) having pixel electrode cells 225 (typically deposited) and the (typically deposited) voltage lead lines 227 from a pixel cell or pixel cell voltage adjustable power source, shown in FIGS. 19D and 19E.

Liquid crystal material 210 is provided between first transparent electrode layer 208 and second transparent electrode layer 212, with the second electrode layer 212 being a full sheet electrode layer (with respect to the transparent pixel electrode cells 225 outer peripheral border). Thus, upon application of a low level voltage (on or off) to the electrode cells 225 through lead lines 227 (depending on the preferred, preset condition) on each individual pixel cell, a desired pixel mode can be achieved due to a change in orientation of the liquid crystal material associated with the activated pixel. Preferably, the deposited 208 electrode layer is deposited directly on the substrate 206 as a thin layer of (ITO) indium-tin oxide or $SnO_2$ by means of conventional depositing techniques such as vacuum evaporation, chemical vapor deposition, electroplating, or other commonly known methods.

The pixel cells mainly defined by the pixel electrode cells and the sandwiched/laminated material associated therewith are preferably arranged in a square matrix which is sufficient in number to achieve the desired degree of ablation precision such as a 1024×1024 pixel array with a pixel size of 100$\mu$ or less being preferred, although other resolutions are also possible with lesser number pixel arrays (e.g., 512×512) and larger pixel sizes (e.g., 100$\mu$ to 150$\mu$).

FIG. 19A further illustrates irregular pixel latent pattern 218 formed in active matrix 202 which is differentiated by the lighter shaded pixel area of pattern 218 provided in the mask (transparent-transmission state) as compared to the darker shaded pixel area 220 (non-transparent non-transmission). For illustrative purposes, there is provided in FIG. 19C, the total volumetric ablation pattern 222 with the three dimensional topography associated with the irregular pixel pattern 218 presented for forming the deepest ablation pattern shown. Each topography level representation (T1 to T7) preferably corresponds to a single volumetric ablation segment or pulse application of the entire ablation volume (shown schematically as each ablation segment would, in a preferred embodiment, correspond with the ablation depth characteristic of the laser which, for a full duty cycle, is often around 0.21$\mu$ to 0.25$\mu$ and thus would typically involve many more layers than the 7 shown). The designation BS is in reference to a best sphere determination as discussed in the above noted U.S. Pat. No. 6,129,722, while MD references the maximum ablation depth involved for this ablation pattern.

In a preferred embodiment, the liquid crystal material 210 provides a twisted nematics (TN) effect on the polarized light 216 passing through matrix 202. With a twisted nematic liquid crystal material, the polarization vector of the incoming light is rotated by a quarter turn ¼ (90 degrees) by the liquid crystal molecules through the natural physical twisted nematics effect produced by the liquid crystal molecules. In other words, liquid nematic substance 210 (typically sealed off by a peripheral frame structure surrounding or abutting the electrode material and sandwiched between the substrate supports) is used as a rotator layer and is placed inside between the two electrodes 208 and 212 as well as between the first and second substrates 206 and 214 and also between polarizers 226 and 228. The second polarizer 228 is designed in one embodiment to have a polarization vector that is 90° offset from that of the first polarizer. In this preferred embodiment, when no voltage is applied on a pixel, the polarization vector of the incoming light is rotated by the liquid crystal molecules through the twisted nematic effect so as to have the rotated polarized light oriented for passage through the 90° offset second polarizer. Thus, the second polarizer, placed at the output side of the liquid crystal mask, is used to transmit the light (normally on).

On the other hand, with the first and second polarizers in a 90° offset relationship, when a proper voltage is applied to a pixel cell, the crystal liquid molecules tend to align with the electric field, such that the twisted nematic effect is lost and thus the polarization vector of the incoming light will be unchanged (i.e., not rotated). The light will therefore be rejected (off) by the output polarizer as its polarization vector is not aligned with the non-twisted UV energy. Alternatively, the first and second polarizers can be arranged to have their polarization vector initially aligned in which case the second polarizer will be normally off (the twisted light is blocked) and upon an electric field application the second polarizer will allow for transmission of the untwisted, polarized light traveling thereto.

Thus during operation of the laser system, laser light beam 111 is directed to expander 218 and then to collimator 219 to distribute and lower the energy per unit area prior to the beam being applied to the liquid crystal mask. The first UV grade polarizer optic component 226 associated with mask 222 (see FIG. 19A) is placed upstream of the liquid crystal material and is suited for handling the relatively high energy densities associated with the UV light beam 211 such as the preferred 193 nm. The first polarizer 226 which the light beam reaches is transparent to the ultraviolet light and is used to polarize the excimer laser beam such that the light beam exiting the polarizer oscillates on a defined plane (e.g., has a common polarization vector) according to the characteristics and orientation of the polarizer optic. The beam is then directed through the UV mask to achieve the desired pattern and then sent through focusing lens 224 and then to the turning mirror where it is directed to the desired ablation location. Mask system 200 shown in FIG. 22 represents a compact optical assembly that can be made as an assembled unit within a common support housing (similar to a telescope housing) and is thus readily inserted in, and removed from, the optical path of the laser. The arrangement shown in FIG. 22 is convenient from the stand point of easy maintenance and compactness although other arrangements maintaining the function of presenting to the ablated surface an active mask generated ablation pattern, are suited for use herein.

With respect to the earlier described laser delivery system of FIG. 8, reliance could be placed on altering the flying spot pattern in an effort to compensate for interpreted tilts and the possibility of undesirable density pattern variations. In other words the number of hits of a flying spot can be altered with the knowledge of the tilt information to compensate the degree of ablation in that area determined by the tilt determination system described above. However, this is a less preferred technique as it would involve limited situations such as extended, common position tilts or a correction program for an initially tilted eye at the point reference parameter capture.

Rather than reliance on the above described liquid crystal based active mask, reliance can be placed on an electro-optical mask as described in the above noted U.S. Ser. No. 09/598,227 application such as an electrochromic mask shown schematically in FIGS. 20A, 20B and 20C. FIGS. 20A and B illustrate schematically the relationship wherein excimer laser 110 is directing unpolarized light 111 to the electro-optical cell 205 (forming one on of many pixel cells in active mask 222). In FIG. 20A the voltage source is off such that the electro-optical cell 225 is in a non-transmitting or off mode.

The electromagnetic energy 111 (e.g. UV light) coming form the excimer laser head 110 is oscillating in all directions and then goes to the electro-optical matrix mask but it can not pass through if no voltage is applied across the electrode layers as shown in FIG. 20B. However, in the transmission pixel cell state shown in FIG. 20C when voltage is applied, light is exposed onto the projecting zone as the pixel is in a bleached (or partially transparent) state.

FIG. 20C provides a schematic presentation of the electro-optical properties of the electrochromic cell 205 contained in mask 222 which has all of its components transparent when the cell is in an uncolored state. As shown in FIG. 20C, the electrochromic cell 205 features outer support substrates 206 and 214, with each being a UV grade substrate such as fused silica, sapphire or quartz when the electromagnetic energy is in the non visible, ultraviolet spectrum and electrochromic element 220. As represented in FIG. 20C, an electric field producer 207 is in electrical communication with deposited electrode sheets 208 and 212 with the illustrated segment of sheet 208 in FIG. 20C representing a pixel segment of sheet 208. By passing a current through the cell through use of electric field generator 207, the coloration of the cell can be achieved and, hence the absorption quality of the cell with respect to incoming electromagnetic energy. The degree of coloration can be controlled by the amount of charge passed through the cell and for a bistable electrochromic material the color state remains after switching off the voltage. To bleach the device, the polarity across the cell is reversed via the electric field generator. Accordingly, an active mask having a plurality of such cells can be adjusted between laser pulses to achieve a desired series of ablation segments leading up to the desired ablation volume pattern. Also, as described above the transmission state of individual pixel cells can be altered when the tracking system detects a tilt in the eye such that the density gradient in the applied area will not be skewed due to the tilt.

Reference is now made to FIGS. 21A, 21B and 21C which illustrate another preferred mask 222 described in the above noted U.S. patent application Ser. No. 09/598,227. FIG. 21A illustrates a cut away section of mask 222 which comprises a multi-stack substrate-dispersed liquid crystal mask having a plurality of pixel cells with one schematic cell shown by reference 300 in FIGS. 21B and 21C. FIG. 21B schematically illustrates cell 300 when in an "off" or non-transmission state. As seen in FIG. 21B, incoming unpolarized electromagnetic energy 302 (e.g., ultraviolet energy such as that output by an excimer laser with for example, a wavelength of 193 nm) passes through a first UV grade support substrate 301 and then through the transparent first deposited electrode layer 304 whereupon it passes into first substrate dispersed liquid crystal layer 306 having randomly oriented liquid crystal bubbles (i.e., the liquid crystal directors of bubbles 308 being randomly distributed due to voltage source 310 being in an off state) within substrate. Second electrode (e.g., ITO) layer 314 is followed by second substrate-dispersed liquid crystal layer 316 (which is materially subjected to an electric field as shown by the cell illustration in FIG. 21C), then third electrode layer 326 and then third substrate dispersed liquid crystal layer 328. Second support plate 303, (which preferably corresponds with last support plate 301) is placed so as to sandwich the fourth electrode layer 334 between it and layer 328. While FIG. 21A features a monolithic unit, a series of individual and self contained mask plates could be used which together achieve the added blocking function described with respect to FIGS. 21B and C.

As shown in FIG. 21B because of the random orientation of the directions in bubbles 308 within the encapsulating substrate 312, the incoming electromagnetic radiation is then scattered as represented by FIG. 21B whereupon a substantial amount of the energy is blocked. Due to the random orientation, some electromagnetic radiation might pass through second deposited electrode layer 314 and into second, intermediate substrate-dispersed liquid crystal layer or cell component 316 having liquid crystal bubbles 318 dispersed within encapsulating substrate 320 (preferably 318 and 320 corresponding material wise with 308 and 312). The directors 322 are oriented perpendicular to the electromagnetic confronting face of the cell due to the electric field generated by electric field generator 324.

For any rays making it through layer 306, their direction will be such that their angle of reflection will result in their further deflection within the intermediate cell 316. This arrangement will orient any such random leakage ray so as to prevent energy from transmitting through cell 316 and out through the next in line deposited electrode layer 326 and further blocking cell component 328, such that all or essentially all of the transmitted energy is not allowed through third substrate-dispersed liquid crystal layer 328 (comprised of randomly oriented bubbles 330 within substrate 332) and the fourth in line deposited electrode layer 334. As with substrate-dispersed liquid crystal (e.g., an electropolymer dispersed layer) 306, layer 328 has random bubbles as voltage source 310 is in a non-electric field generation state. FIG. 21B also illustrates first and second substrate plates 301 and 303 which are preferably formed of UV grade synthetic fused silica (UV GSFS (SiO$_2$)).

FIG. 21C illustrates cell 300 in a transmission "on" state wherein electromagnetic energy 302 (entering in a common direction with respect to the below described aligned directors of each bubble set) passes freely through cell 300 to a desired projected surface (e.g., the cornea of an eye). As shown in FIG. 21C, in addition to voltage source 324 continuing to maintain intermediate layer or cell component 316 with the directors of bubbles 322 oriented in the desired direction of travel of the electromagnetic energy beam 302, voltage source 310 is placed on such that the directors in bubbles 308 in layer 312 and the directors in bubbles 330 become commonly oriented with the directors in bubbles 322 in intermediate layer 316. Thus, with this arrangement, the electromagnetic radiation (e.g., a pulsed excimer laser output) is free to pass through to achieve a desired ablation effect on a substrate to be ablated.

Accordingly, the individual pixel cells can be controlled as described for the other mask embodiments for determining what portions of the applied laser beam are blocked or allowed through. Also, by linking the mask based laser beam delivery system to the eyetracker there can be made adjustments on the X-Y plane either by shifting the relative position of on/off pixels and/or the turning mirror orientation. Also, like the other above described mask embodiments, eye tilt information provided by the eyetracker can be used to adjust the pixel transmission states to avoid undesirable energy density variations with respect to the intended pulse application area. This includes the above noted compensation techniques of altering the on/off characteristics by duty cycle adjustments or blocking/opening regions off/on in one or more ablation segments/pulse sequences to accommodate the different density effect due to tilt. In other words, certain pixel "on" regions subject to higher energy density than originally designated due to the tilt can be placed off or in a blocking mode, while shadow regions of the tilt can be switched from the originally set blocking mode to a transmission mode. The adjustment in pixel cell transmissiveness can also include assigning pixels with intermediate transmission states in addition to full blocking or full on states. With regard to the bubble dispersion cell in FIG. 21C, this can include removing the random orientation in only one or two of the dispersed bubble substrates to allow an intermediate level of energy applications.

With reference to FIGS. 22 to 25 there is provided a description of a preferred laser delivery system of the present invention which is well suited for accommodating eye tilt in that the laser beam is delivered along an axis which is coincident or parallel with the normal axis of the eye (or whatever eye axis is chosen as the time of initial reference determination to be the one aligned with the laser beam delivery reference axis). FIG. 22 shows a view similar to FIG. 17 except for the introduction of tilt accommodation delivery system 400 which comprises scan mirror 402 and compensating mirror 404. A preferably fixed turning mirror 121 is positioned upstream of scan mirror 402 to accommodate laser beam travel for the typical orientations of a laser. With altered initial alignment of the laser initial beam projection through a repositioning of the entire laser, a direct passage position to scan mirror (at the first focal point of mirror 404) is possible but generally impractical due to the size of the laser and the location it would need to assume. FIG. 23 provides a schematic physical structure view of the system shown in FIG. 22 and provides a schematic illustration of the relative positioning of the scan mirror 402 and elliptical mirror 404 in the optical path of the UV laser beam 111.

Also, in FIG. 22 mask system 200 is shown in dash lines in FIG. 22 as the tilt accommodation laser delivery system 400 is applicable as well to laser delivery systems that are free of the mask system 200 (e.g., a system that would normally rely on an adjustable turning mirror for small or large spot beam adjustments). In the latter case the turning mirror 121 is preferably held stationary when used with system 400 once mirror 121 is properly aligned with respect to scan mirror 402. As described, however, the mask system 200 provides the opportunity to use faster ablating large beam applications with the ablation pattern rapidly and precisely adjusted with the active mask's varying pixel pattern and correspondingly simplifies the tilt accommodation delivery.

In FIG. 22 scan mirror interface 134 is in line between the scan mirror 402 and processing means such as main computer 132 to adjust scan mirror 402 while it maintains its central pivot position at the focal point of ellipsoidal mirror 404. In the preferred embodiment, turning mirror 121 is fixed and the mask is not interlinked with the eyetracking system, but instead changes its pixels in accordance only with the predetermined ablation volume pattern. In this way, a specific pattern is conveyed to the scan mirror 402 which is relied upon to achieve the desired laser delivery accommodation changes to suit tilts in the eye. That is, it is the scan mirror 402 which is adjusted to accommodate for sensed tilts in the eye so as to ensure that the laser beam retains a normal axis relationship with the eye despite any eye tilt. With this preferred arrangement, movement of the head along the X-Y plane is minimized with a head holding means such as a cervical pillow. This is because the ellipsoidal based mirror and scan mirror are preset to fully accommodate a full range of tilt about a predetermined relatively fixed focal point. An eyetracker system analysis for any X-Y shift is thus made only from the standpoint of determining whether the eye is within a suitable parameter values for allowing for a laser shot to take place.

Reference is made to FIGS. 24 and 25 for additional detail as to the accommodation made possible by the ellipsoidal mirror 404 when the eye tilts. FIG. 24 shows an ellipse $E_1$ corresponding with a cross-section through the ellipsoidal mirror with the ellipse's major diameter extending from point H1 to H2 with this distance being preferably based on the microscope's focal length (e.g. 30 cm). The scan mirror 402 is positioned at F1 (e.g. 5 cm down from H1 along the major axis) which is the first focal point along the major axis of ellipse $E_1$ while the second focal point F2 coincides with the curvature center of the cornea having radius $R_c$ (e.g. 25 cm down from H1). The ellipse $E_1$ in FIGS. 24 and 25 is shown tilted (e.g. angle B at 15 to 20 degrees) so as to help accommodate a non-interfering beam segment passage from the fixed turning mirror 121 to the adjustable scan mirror 402. The illustrated ellipsoidal mirror's 404 major cross-section shown in FIG. 26 is arranged so as to generally extend over an upper quadrant of ellipse $E_1$ so as to provide for sufficient beam scan to achieve the aforementioned maximum tilt range for the eye (e.g. a cone of 15 to 30 degrees divergence from a normal vertical central eye axis) corresponding with the initial laser beam reference setting.

In operation, the ablation volume pattern, which is based on a normal non-tilt reference setting, is thus implemented while the eyetracker system monitors the position of the eye both from a tilt and X-Y axis shift adjustment standpoint. Again, the latter being used to determine whether ablation should continue as the design of the ellipsoidal mirror 402 is set up to best operate when no X-Y axis plane shifting is involved.

Through use of an analysis like that described above with respect to FIGS. 12B, 12C and 12D, the angle of tilt in an eye can be determined and can be conveyed as an X-Y plane shift $\Delta U$, for example. The laser beam output from turning mirror 121 is directed to the movable scan mirror 402 positioned at the focal point F1 of mirror 404 such that movement of the scan mirror, in conjunction with the shape of mirror 404 provides for delivery of an angle beam precisely corresponding with the angle of tilt assumed by the eye (angle $\Theta$-based or the shift of eye axis No to position $N_1$ together with, for example, X and Y axis coordinate or a polar angle value for the intersection of axis N1 at angle $\Theta$ with respect to the X-Y plane of the cone base of the range of possible eye tilts with respect to No. Elliptical mirror 404 is thus maintained fixed in position as this relationship allows for scan mirror 402 to simply assume an orientation that places the pre-reflected beam B1 at the proper contact point on the curved mirror 404 to achieve a post reflecting coincident angle beam $B_2$ that is based on the determined eye tilt $\Theta$ value.

In addition to scan mirror 402 and ellipsoidal mirror 404, FIG. 24 provides a more detailed illustration of some of laser system components shown in FIG. 22 with emphasis on the interrelationship between eyetracking system components and the tilt accommodation laser delivery system 400 of the present invention. As noted above, ellipsoidal mirror 404 is dimensioned and arranged such that the fixed upstream turning mirror 121 and scan mirror work together to choose a point on the fixed ellipsoidal mirror such that the beam is directed along an axis coincident to the normal axis of an eye having undergone a tilt.

FIGS. 24 and 25 illustrate the manner in which mirror 404 can readily accommodate for any angle tilt within a predetermined cone shaped range. When the eye tilts (see the left and right tilt reference mark depictions 406 and 408 in FIG. 25 with relation to the non-tilted eye schematic representation 410 for eye 412), there is presented video screen depictions having the pointer reference markers in the positions illustrated in FIG. 25. Thus, using the information conveyed due to the relative relationship of the reference marker points with respect to the original more central reference point (for example) based on the original normal axis intersection at the apex of the eye coinciding with the laser beam reference location, the tilt parameters of the tilted eye can be determined (see the discussion for FIGS. 12D and 12E above as well). This information is then forwarded to the main computer (e.g. along the "tilt signal compensation" communication link) and then from the computer to the scan mirror interface which tilts the mirror 402 (typically along two fixed axis to cover the major axis and minor axis curvature of the mirror 404). The tilt accommodation laser delivery system 400 is thus particularly suited for accommodating a full range of eye tilt, particularly when used in conjunction with the highly effective eyetracker system described above.

Although the present invention has been described with reference to preferred embodiments, the invention is not limited to the details thereof. Various substitutions and modifications will occur to those of ordinary skill in the art following a review of this application, and all such substitutions and modifications are intended to fall within the spirit and scope of the invention as defined in the appended claims.

What is claimed is:

1. An eye laser system, comprising:
    a laser;
    a laser delivery system for delivering a laser beam generated by said laser to an eye;
    an eyetracking system which monitors movement of the eye and conveys eyetracking information to said laser delivery system, said eyetracking system including a non-invasive eye tilt reference marker.

2. The laser system as recited in claim 1 wherein said reference marker is a reference marker that projects an energy beam so as to reflect off the iris of the eye.

3. The laser system as recited in claim 2 wherein said reference marker includes a plurality of points arranged concentrically about the pupil of the eye.

4. The laser system as recited in claim 3 wherein there are at least three reference marker points reflected from the iris.

5. The laser system as recited in claim 4 wherein there are four reference marker points.

6. The laser system as recited in claim 5 wherein said eyetracker system includes a video frame developer and means for analyzing captured video frames.

7. The laser system as recited in claim 6 wherein said video frame developer includes a frame reference component that includes X and Y axis extensions and said four reference marker points land on respective extensions when the eye is in a reference setting.

8. The laser system as recited in claim 3 wherein said reference marker further comprises a ring illuminator.

9. The laser system as recited in claim 8 wherein said reference marker generates visible light that provides surgical illumination.

10. The laser system as recited in claim 1 wherein said reference marker provides a concentrically arranged pattern on said pupil which is concentric with said pupil.

11. The laser system as recited in claim 1 wherein said reference marker includes point marker lights positioned circumferentially about the laser beam path.

12. The laser system as recited in claim 11 wherein said point marker lights operate in the visible light spectrum.

13. The laser system as recited in claim 1 wherein said reference marker reflects a pattern on said eye that is concentric with respect to said pupil and further comprising means for determining eye tilt based on any non-concentric adjustment between a pupil reference point and said pattern.

14. The laser system as recited in claim 13 wherein said pattern includes a four equally spaced point pattern.

15. The laser system as recited in claim 13 wherein said analyzing means determining means for determining a tilt angle of said eye.

16. An eyetracker system for use in determining eye tilt comprising a reference marker generating means for producing on an eye iris a pattern that indicates an eye tilt upon a tilt in said eye and means for generating an eye tilt existence signal to a laser delivery system.

17. The eyetracker system as recited in claim 16 wherein said pattern includes at least four equally spaced light points projected on the iris of an eye.

18. The eyetracker system as recited in claim 16 wherein said eye tilt determination means includes means for determining a tilt angle of said eye.

19. A laser delivery system for use in an eye laser surgery system, comprising a scan mirror and an ellipsoidal mirror positioned to accommodate eye tilt while delivering energy derived from an eye surgery laser.

20. A laser system comprising the laser delivery system recited in claim 19 and further comprising a laser.

21. A laser system as recited in claim 20 and further comprising an eyetracker system with means for monitoring eye tilt.

22. The laser system of claim 20 wherein said laser is a laser outputting ultraviolet light at a wavelength of 193 nm.

23. The laser system of claim 20 wherein said laser has an energy level of 400 mj or higher.

24. A laser system for use in an eye laser system, comprising
    a scan mirror,
    an ellipsoidal mirror positioned to accommodate eye tilt,
    a laser, and
    an eyetracker system with means for monitoring eye tilt, wherein said eyetracker system comprises reference point lights positioned so as to reflect off the iris so as to convey pupil adjustments through variations in a relative position of said point markers with respect to said pupil.

25. A laser system for use in an eye laser system, comprising
    a scan mirror,
    an ellipsoidal mirror positioned to accommodate eye tilt,
    a laser, and
    an eyetracker system with means for monitoring eye tilt, wherein said eyetracker system comprises means for generating a concentric pattern on the iris of the eye being treated.

26. A laser system comprising
    a laser delivery system comprising
    a scan mirror, and
    an ellipsoidal mirror positioned to accommodate eye tilt; and
    a laser and an active crystal mask positioned in an optical path of said laser.

27. An eye ablation system, comprising:
    a tilt accommodation eye ablation energy delivery system which avoids uneven energy distribution in a region of ablation energy contact of the eye,
    an eye tilt tracker, and said delivery system comprising means for adjusting an angle of application of the eye ablation energy in conjunction with information provided by said eye tilt tracker.

28. The eye ablation system of claim 27 wherein said scan mirror is positioned at a focal point of the ellipsoidal mirror.

29. The eye ablation system of claim 27 further comprising a laser outputting an energy beam suited for eye tissue ablation.

30. The eye ablation system of claim 27 wherein said eye tilt tracker includes a non-invasive eye tilt reference marker.

31. The eye ablation system of claim 30 wherein said reference marker is a reference marker that projects reference marker energy to reflect off an iris of the eye.

32. An eye surgery laser system, comprising:
   a laser outputting an energy beam suited for ablating eye tissue;
   an energy beam optical path for delivering the energy beam to an eye which comprises adjustment means for making adjustments in the energy beam traveling in said optical path;
   an eye tilt monitor; and
   an interface which receives data from said eye tilt monitor and outputs to said adjustment means adjustment data to compensate for eye tilt.

* * * * *